(12) United States Patent
Mignet et al.

(10) Patent No.: US 11,291,630 B2
(45) Date of Patent: Apr. 5, 2022

(54) GELLING COMPOSITIONS FOR TREATING MALIGNANT TUMOURS AND/OR PREVENTING TUMOUR RECURRENCE

(71) Applicants: Centre National de la Recherche Scientifique (CNRS), Paris (FR); Université de Paris, Paris (FR); Assistance Publique-Hopitaux de Paris, Paris (FR); Ecole Nationale Superieure de Chimie de Paris, Paris (FR); Institut National de la Sante et de la Recherche Medicale (INSERM), Paris (FR)

(72) Inventors: Nathalie Mignet, Clamart (FR); Vincent Pierre-Marie Boudy, Paris (FR); Johanne Seguin, Kremlin Bicêtre (FR); Daniel Scherman, Paris (FR); Yoran Beldengrun, Zurich (CH)

(73) Assignees: Centre National de la Recherche Scientifique (CNRS); Université de Paris; Assistance Publique-Hopitaux de Paris; Ecole Nationale Superieure de Chimie de Paris; Institut National de la Sante et de la Recherche Medicale (INSERM)

(*) Notice: Subject to any disclaimer, the term of this patent is extended or adjusted under 35 U.S.C. 154(b) by 0 days.

(21) Appl. No.: 15/760,249

(22) PCT Filed: Sep. 16, 2016

(86) PCT No.: PCT/EP2016/072038
§ 371 (c)(1),
(2) Date: Mar. 15, 2018

(87) PCT Pub. No.: WO2017/046369
PCT Pub. Date: Mar. 23, 2017

(65) Prior Publication Data
US 2019/0192430 A1 Jun. 27, 2019

(30) Foreign Application Priority Data
Sep. 16, 2015 (EP) .................................. 15306426

(51) Int. Cl.
*A61K 9/06* (2006.01)
*A61K 31/282* (2006.01)
(Continued)

(52) U.S. Cl.
CPC .............. *A61K 9/06* (2013.01); *A61K 9/0019* (2013.01); *A61K 9/0024* (2013.01);
(Continued)

(58) Field of Classification Search
CPC ........ A61K 9/0019; A61K 47/10; A61K 9/06; A61K 47/36; A61K 9/0024; A61K 47/34; A61N 2005/1087
See application file for complete search history.

(56) References Cited

U.S. PATENT DOCUMENTS 5,124,151 A * 6/1992 Viegas ................. A61K 9/0019
424/422
2002/0192289 A1 12/2002 Zheng et al.
(Continued)

FOREIGN PATENT DOCUMENTS

WO 2006086775 A2 8/2006

OTHER PUBLICATIONS

Frangioni, John V., "New Technologies for Human Cancer Imaging", Journal of Clinical Oncology, vol. 26, No. 24, Aug. 20, 2008, pp. 4012-4021.
(Continued)

*Primary Examiner* — Jianfeng Song
(74) *Attorney, Agent, or Firm* — Lerner, David, Littenberg, Krumholz & Mentlik, LLP

(57) ABSTRACT

The present invention relates to gelling compositions, which changes from liquid state to gel state in function of tem-
(Continued)

perature comprising: at least a poloxamer or mixture of poloxamers; at least a gelling agent; and at least an anticancer agent. Said compositions are advantageously used for local administration of an anticancer agent. Said compositions are useful for size-reduction of a tumour before surgical removal of said tumour, for preventing tumour recurrence after surgical removal of a tumour, and/or treating small tumours. They are therefore useful for the treatment of cancer, preferably a cancer of a wall of the digestive system or a gynaecologic cancer. The present invention also relates to a method for preparing said gelling compositions.

6 Claims, 10 Drawing Sheets

(51) Int. Cl.
  A61K 31/513 (2006.01)
  A61K 47/34 (2017.01)
  A61K 47/36 (2006.01)
  A61K 47/02 (2006.01)
  A61N 5/10 (2006.01)
  A61P 35/00 (2006.01)
  A61K 47/10 (2017.01)
  A61K 9/00 (2006.01)
  A61K 31/555 (2006.01)
  A61K 31/519 (2006.01)
  A61K 31/37 (2006.01)
  A61K 33/243 (2019.01)

(52) U.S. Cl.
  CPC ............ *A61K 31/282* (2013.01); *A61K 31/37* (2013.01); *A61K 31/513* (2013.01); *A61K 31/519* (2013.01); *A61K 31/555* (2013.01); *A61K 33/243* (2019.01); *A61K 47/02* (2013.01); *A61K 47/10* (2013.01); *A61K 47/34* (2013.01); *A61K 47/36* (2013.01); *A61N 5/10* (2013.01); *A61P 35/00* (2018.01); *A61N 2005/1087* (2013.01)

(56) References Cited

U.S. PATENT DOCUMENTS

2009/0098200 A1    4/2009   Temtsin Krayz et al.
2011/0301456 A1   12/2011   LeClaire et al.
2013/0195988 A1*   8/2013   Duan .................. A61K 9/0019
                                                                           424/497

OTHER PUBLICATIONS

International Search Report for Application No. PCT/EP2016/072038 dated Nov. 23, 2016, 4 pages.
Krupka et al., "Injectable Polymer Depot Combined With Radiofrequency Ablation for Treatment of Experimental Carcinoma in Rat", Investigative Radiology, vol. 41, No. 12, Dec. 2006, pp. 890-897.
Nie et al., "Thermoreversible Pluronic® FI27-based hydrogel containing liposomes for the controlled delivery of paclitaxel: in vitro drug release, cell cytotoxicity, and uptake studies", Internal Journal of Nanomedicine, Jan. 2011; 6:151-166.
Sjövall et al., "Loco-regional Recurrence from Colon Cancer: A Population-based Study", Annals of Surgical Oncology, vol. 14, Issue 2, pp. 432-440, Feb. 2007.
Yang et al., "A novel mixed micelle get with thermo-sensitive property for the local delivery of docetaxel", Journal of Controlled Release 135, Apr. 2009, pp. 175-182.
Zeng et al., "Influence of additives on a thermosensitive hydrogel for buccal delivery of salbutamol: Relation between micellization, gelation, mechanic and release properties", International Journal of Pharmaceutics, Jun. 5, 2014, 467(1-2):70-83.

* cited by examiner

GELLING COMPOSITIONS FOR TREATING MALIGNANT TUMOURS AND/OR PREVENTING TUMOUR RECURRENCE

CROSS REFERENCE TO RELATED APPLICATIONS

The present application is a national phase entry under 35 U.S.C. § 371 of International Application No. PCT/EP2016/072038 filed Sep. 16, 2016, published in English, which claims priority from European Patent Application No. 15306426.6 filed Sep. 16, 2015, all of which are incorporated herein by reference.

TECHNICAL FIELD

The present invention relates to gelling compositions comprising an anticancer agent advantageously for local administration. Said compositions are useful for size-reduction of a tumour before surgical removal of said tumour, and/or for preventing tumour recurrence after surgical removal of a tumour, and/or for treating small tumours which could then advantageously avoid surgery. They are therefore useful for the treatment of cancer, preferably a cancer of a wall of the digestive system or a gynaecologic cancer. The present invention also relates to a method for preparing said gelling compositions.

BACKGROUND

Cancer is nowadays a major public health concern. Most conventional treatments of cancer include chemotherapy, either as a primary intention treatment, or as an adjuvant treatment to surgery. However, chemotherapy often involves side effects, occurring due to systemic administration of the drug (either when administered by intravenous or oral route). Such side effects are often very painful to the patient, hence limiting the use of high doses of anticancer agents, and thus affecting the overall efficacy of the treatment in some instances.

In particular, for colorectal cancer (CRC), which is the cancer with second highest mortality and third highest incidence in France, surgery is the most frequent treatment option, but locoregional post-surgical recurrence remains a major problem and occurs at 11% of colorectal cancer patients (Sjövall et al. *Ann. Surg. Oncol.* 14 (2007) 432-40; doi:10.1245/s10434-006-9243-1), which is the reason why adjuvant chemotherapy is usually used after surgery to eliminate residual cancer cells and prevent recurrent tumour growth. The most frequent combination chemotherapy is the FOLFOX4 therapy, which combines intravenous administrations of Oxaliplatin, Leucovorin (i.e. Folinic Acid) and 5-Fluorouracil (5-FU) (N.C. Institute, Colon Cancer Treatment). Currently, all formulations tested for this application act systemically, resulting in undesired side-effects.

Similar problems are faced by patients suffering from cancers of a wall of the digestive system such as stomach or oesophagus cancer, or gynaecologic cancer such as ovarian or womb cancer, including cervix cancer.

There is therefore a need for alternative formulations exhibiting limited patients discomfort due to side effects caused by systemic delivery of the chemotherapy, and with an improved bioavailability, so as to improve the general efficacy of chemotherapies.

In recent years, efforts have been made to develop alternative adjuvant treatments with reduced side effects and easy administration, in particular treatments aimed at preventing tumour recurrence after surgical removal of a colorectal tumour.

To this end, compositions for local administration are preferred, because it allows direct delivery to the pathological site, which increases the drug's bioavailability, and avoids systemic circulation. Such a treatment strategy is meant to result in reduced side-effects, and to allow for a better control of the on-site concentration delivery of the anticancer agent.

For instance, Yang et al (J. Control. Release. 135 (2009) 175-82. doi:10.1016/j.jconrel.2009.01.007) reported a poloxamer-based in-situ gelling hydrogel comprising docetaxel as the anticancer agent to be administered by intra-tumoral, peritumoral and subcutaneous injection, for treating subcutaneous ovarian cancer, involving local administration of docetaxel. Said gelling hydrogel releases 70% of its docetaxel content after 156 h. It allows for full tissue coverage, and may be injected non-invasively with a needle. However, this hydrogel exhibits limitations, such as absence of bioadhesive properties.

Worth mentioning is also the PLGA-based (poly(lactic-co-glycolic acid)-based) gelling hydrogel developed by Krupka et al. (Invest. Radiol. 41 (2006) 890-7. doi:10.1097/01.rli.0000246102.56801.2f), which comprises carboplatin as the anticancer agent, and a chemosensitizer. This PLGA-based gelling hydrogel aims at treating subcutaneous colorectal carcinoma. The goal is to make a depot of the formulation, meaning that it is a highly visqueous formulation which is not aimed to be sprayed.

Application US 2002/19289 discloses compositions useful for treating cancer, however aiming at blocking the tumor blood vessels, and more particularly at preventing angiogenesis. Said compositions contain a polymer able to form a gel by crosslinking upon photoinitiating, electromagnetic initiation or by temperature modification. The crosslinked gel prevents the blood from circulating into the blood vessels, thus leading to necrosis of same. Thus, the compositions of US 2002/19289 differ significantly both in terms of composition (a combination of poloxamers with a gelling agent is not disclosed) and of intended use. In addition, no composition is exemplified.

Application US 2002/192289 discloses compositions useful for treating cancer, aiming both an locally releasing a therapeutic agent such as an anticancer agent, and to generate a vascular embolization. The compositions of US 2002/192289 are thermosensitive, and form a gel at the body temperature. Said compositions may comprise a poloxamer, in particular in combination with PVP. However, PVP (Polyvinylpyrrolidone) is not a gelling agent. PVP(E)201 is listed as firming, stabilizing and dispersing agent in Codex alimentarius—Common Program of the World Health Organization (WHO) and Food and Agriculture Organization (FAO). Also, it is known to the one of skill in the art that PVP is inserted in cosmetic products as hair fixative, binder, antistatic, emulsifier, etc. . . . . Indeed, PVP allows adjusting the viscosity (see for instance the website of BTChemicals), but it is not a gelling agent. Therefore, US 2002/192289 does not teach using a combination of poloxamers and a gelling agent.

Application US 2011/301456 does not disclose compositions which neither comprise any anticancer agent nor any gelling agent.

Application WO 2006/086775 concerns delivery formulation for local application for reducing leakage. The compositions of WO 2006/086775 are in particular useful for treating cancer. However, the therapeutic agent is an active vector useful in gene therapy. In addition, the compositions of WO 2006/086775 contain a blocking agent, so that administration of said compositions results in the viscosity of the blocking agent increasing to at least 100 cP. Said blocking agent is obtained through forming gel "balls". The compositions of WO 2006/086775 are thus a dispersion of gelified particles. Such an inhomogeneous composition could not be administered by spraying for instance. Finally, WO 2006/086775 does not teach using a combination of poloxamers and a gelling agent.

Also, application discloses compositions, aiming at improving the water solubility of some therapeutic agents, such as docetaxel. However, said compositions are provided as dry compositions, and are to be administered orally, fir systemic administration. Therefore, there is a need for more effective cancer treatments, in particular for reducing the size of tumours prior to surgery, and/or for preventing tumour recurrence after surgical resection, and/or for treating small tumours which could then advantageously avoid surgery, which would also result in cancer recurrence. Not only should said treatments increase the life expectancy of the patient, but they should also improve their comfort, as compared to prior art treatments.

The invention thus aims at providing compositions to be administered via local route, in particular for use in the treatment of tumour recurrence after surgical resection and/ or for treating small tumours which could then advantageously avoid surgery.

The present invention also aims at providing compositions to be administered via local route useful in a treatment prior to surgery for reducing the size of the tumour.

To this end, it is proposed gelling compositions comprising at least one poloxamer, a gelling agent and an anti-cancer agent. Undesired side-effects are thus reduced for two reasons: local application (at least partly) avoids systemic circulation of the drug. Bioavailability and on-site concentration control of the anticancer agent are also improved compared to other administration routes (in particular systemic routes). In addition, the doses required for the same therapeutic effect may be lowered, as the anticancer agent is directly bioavailable on the targeted site of action, as compared with conventional systemic treatments.

In addition, the gelling compositions are prepared, packaged and stored at a temperature at which they are in liquid form. Compared to preformed gels, their lower viscosity facilitates the manufacturing process (sterilization, packaging, storage). They also allow for several administration routes, such as spraying (spray), spreading or injection. Finally, their adhesion and erosion properties can be tuned very easily (Zeng et al, Int J Pharm. 2014 Jun. 5; 467(1-2): 70-83. doi: 10.1016/j.ijpharm.2014.03.055).

SUMMARY OF THE INVENTION

In a first aspect, the present invention thus relates to a gelling composition comprising:
at least a poloxamer or mixture of poloxamers;
at least a gelling agent; and
at least an anticancer agent.

In another aspect, the present invention relates to a solid composition for extemporaneous formation of a gelling composition of the invention, comprising:
at least a poloxamer or mixture of poloxamers;
at least a gelling agent;
at least an anticancer agent; and
more than 5 wt % of water.

In a further aspect, the present invention is drawn to the composition of the invention for use as a medicament, in particular for the treatment of cancer, preferably a cancer of a wall of the digestive system or a gynaecologic cancer.

In another aspect, the present invention relates to the use of the gelling composition of the invention for the manufacture of a medicament, in particular for the treatment of cancer, preferably a cancer of a wall of the digestive system or a gynaecologic cancer.

In yet another aspect, the present invention concerns a method for treating cancer, preferably a cancer of a wall of the digestive system or a gynaecologic cancer, comprising administering to a patient in need thereof, preferably via local administration, a therapeutically effective amount of the gelling composition of the invention.

According to another aspect, the present invention relates to a kit comprising at least:
a first composition comprising the gelling composition of the invention, and
a second composition comprising at least another therapeutic agent, in particular another anticancer agent, an anti-vascular agent or an antiangiogenic agent.
for simultaneous, staggered or sequential use, for use as a medicament, in particular for the treatment of cancer, preferably a cancer of a wall of the digestive system or a gynaecologic cancer.

According to another aspect, the present invention relates to methods for preparing the gelling compositions of the invention.

Definitions

As used herein, the percentages refer to percentages by weight relative to the total weight of the composition, unless otherwise indicated. With regard to the gelling compositions, the amount of water added is such that the total of the components and water is equal to 100 wt % relative to the total weight of the composition.

As used herein, the value ranges form "xy" or "x to y" or "between x and y" include limits x and y, and the integers between these limits. For example, "1-6" or "between 1 and 6" means the integers 1, 2, 3, 4, 5 and 6. The preferred embodiments include each integer taken individually in the value range, and any sub-combination of these integers. For example, the preferred values for "1-6" may include integers 1, 2, 3, 4, 5, 6, 1-2, 1-3, 1-4, 1-5, 2-3, 2-4, 2-5, 2-6, etc.

As used herein, a "gelling composition" is understood as a composition capable of gelling at a given temperature, particularly in contact with the mucosa of the wall of the digestive system (such as colon, intestine, stomach or oesophagus) or of the gynaecologic sphere (such as ovaries mucosa, fallopian tubes, womb mucosa, cervix and vagina mucosa). The gelling compositions of the present invention are preferably "pharmaceutical compositions", that is to say that they are suitable for therapeutic use to a subject, such as a human patient. The gelling compositions of the invention are advantageously thermosensitive.

As used herein, "thermosensitive" or "temperature sensitive" refers to a composition which is a liquid or a low viscosity solution (i.e. viscosity less than 500 cps at 25° C. at a shear rate of about 0.1/second) at a low temperature (between about 0° C. to about 10° C.), but which is a higher viscosity (i.e. viscosity less than 10,000 cps at 25° C. at a shear rate of about 0.1/second) gel at a higher temperature (between about 30° C. to about 40° C. such as at about 37° C.).

The "gelling temperature" or "temperature of gelation" ($T_g$) of a composition is known in the art. It corresponds to the temperature at which gelation of the composition occurs. It is commonly measured using differential scanning calorimetry (DSC) either alone or combined with the determination of rheological parameters such as viscoelastic shear storage modulus G' and shear loss modulus G".

"Administration", or "to administer" means the step of applying (i.e. administering) a (pharmaceutical) composition to a subject. The compositions disclosed herein are "locally administered" by e.g. parenteral, either by injection within or in the vicinity of the tumour or intra-arterial injection in a tumour blood vessel or in a blood vessel irrigating the tumour, or by spraying or spreading the composition directly on the tumour or at the site of resection. In particular, administration by injection is applied to a targeted site avoiding systemic administration of the therapeutic agents. As used herein, the targeted site is in particular the tumour (for instance for sized reduction of a tumour), or the area just around the tumour or resected tumour (in particular for tumour recurrence prevention).

In the present invention, a "therapeutic agent" means an active pharmaceutical ingredient (API) which has a therapeutic use or benefit when administered to a patient. The therapeutic agent can be for example an anticancer agent. Preferably, the therapeutic agent is a chemical agent, i.e. it is a "small" molecule, as understood in the art. In particular, the therapeutic agent is not a vector useful in gene therapy.

As used herein, "sustained release" means that the therapeutic agent (i.e. a anticancer agent and/or) contained in a pharmaceutical and/or gelling composition (such as a gelling composition comprising a poloxamer) is released from the pharmaceutical composition over a period of time of between a few minutes and about 3 months, preferably over a period of 1 h to 1 month, for instance from 1 h to 1 week.

As used herein, the term "poloxamer" refers to a tri-block copolymer comprising or consisting of a central polyoxypropylene chain (also called polypropylene glycol, PPO) grafted on either side by a chain of polyoxyethylene (also known as polyethylene glycol, POE). Poloxamers thus comprise a central hydrophobic chain of poly(propylene oxide) surrounded by two hydrophilic chains of poly (ethylene oxide) (PEO-PPO-PEO block copolymer). Poloxamers are generally designated by the letter "P" (for poloxamer) followed by three digits: the first two numbers multiplied by 100 gives the molecular weight of polyoxypropylene heart, and the last digit multiplied by 10 gives the percentage of content polyoxethylene. For example, P407 (also known as Pluronic® F127) is a poloxamer including the heart in a polyoxypropylene molecular mass of 4000 g/mol and a polyoxyethylene content of 70%. P407, when solubilized in aqueous solution has good solubilizing capacity, low toxicity and shows thermoreversible properties. Without wishing to be bound by theory, it is believed that the hydrophobic PPO block of the poloxamer is dehydrated, which leads, due to entropic reasons, to micellisation of the polymer. Gelation, thus strong increase in viscosity, is attributed to ordered packing of micelles. Gelation is reversible upon cooling. The liquid-solid transition temperature depends on various parameters. Moreover, due to their amphiphilic character, poloxamers are able to solubilise both hydrophobic and hydrophilic compounds.

As used herein, the term "gynaecologic cancer" is understood as a cancer of the gynaecologic sphere, in particular ovarian cancer or womb cancer, including cervix cancer.

As used herein, the term "cancer of a wall of the digestive system" is understood as including any cancer involving a wall of the digestive system, such as colon, intestine, stomach or oesophagus. In particular, a "cancer of a wall of the digestive system" is understood as being selected from the group consisting of colorectal cancer, stomach cancer and oesophagus cancer, and is preferably a colorectal cancer.

As used herein, the "site of resection" corresponds to the remaining tissue around (or in the vicinity of) the tumour once it has been resected.

As used herein, the "area of interest" or the "area of application" or the "area to be treated" corresponds to the site of resection in case of post-surgery treatment, or corresponds to the tumour in case of size reduction of the tumour prior to surgery.

As used herein, a "patient" or "subject" is understood as a mammal, preferably a human.

As used herein, the "bioadhesion" of a composition corresponds to the adhesion of said composition to biological tissues, in particular the tissues of the area to be treated. The gelling compositions of the invention preferably exhibit a good bioadhesion.

As used herein, a "small tumour" is a tumour not visible or detectable by usual techniques such as echography, PET imaging, CT or MRI with or without a contrast agent, in particular not visible by the surgeon during resection, even with the use of intraoperative imaging. Typically, such a small tumour has a volume of less than 1 mm$^3$. Indeed, the best resolution of these usual techniques of three-dimensional detection of cancer anywhere in the body is 1 mm$^3$ (Frangioni J Clin Oncol 25 (2008) 4012-4021).

DETAILED DESCRIPTION OF THE INVENTION

The present invention concerns a gelling composition comprising:
at least a poloxamer or mixture of poloxamers;
at least a gelling agent; and
at least an anticancer agent.

Typically, the gelling composition of the invention comprises more than 5 wt % water, even more preferably more than 10 wt % water, even more preferably between 15 wt % and 70 wt % of water. Said water is preferably sterile water (such as ultrapure water or water for injection).

Such "aqueous" compositions are typically homogeneous.

The gelling compositions of the present invention are advantageously thermosensitive. Preferably, the gelling temperature or temperature of gelation of the composition of the invention is of between 20° C. and 40° C., more preferably in contact with mucous membranes, in particular at a temperature between 22° C. and 38° C., for example between 24° C. and 36° C.

Useful poloxamers according to the invention are temperature sensitive poloxamers, which according to their concentration in solution are in the liquid state at room temperature, and in particular between 2° C. and 20° C., and in the state of gel at a temperature greater than or equal to the gelling temperature (Tg), especially under physiological conditions, and in particular between 20° C. and 40° C.

Temperatures of gelation of poloxamers (Tg) can be determined according to conventional methods as explained above or are available in reference works such as the Handbook of Pharmaceutical Excipients.

Poloxamer 407, poloxamer 188 or mixtures thereof are particularly preferred.

More particularly, these poloxamers are present in sufficient concentration in the compositions of the invention to allow gelation when the temperature is greater than or equal to its gelation temperature (Tg), particularly under physiological conditions. Typically, the compositions of the present application thus comprise from 12 wt % to 30 wt %, preferably from 15 wt % to 28 wt %, of poloxamers relative to the total weight of the composition.

The gelling compositions of the invention contain a gelling agent. Said gelling agent aims at reinforcing the 3D-structure of the composition, so as to modify the mechanical, gelling, bioadhesion and release properties of the composition. For instance, the content of the gelling agent impacts the gelling temperature. In some instances, the content of the gelling agent impacts the sustained release profile of the composition.

Preferably, the gelling agent is selected from the group consisting of chitosan and derivatives thereof, for example chitin, carrageenan and derivatives thereof, for example carrageenan with a sulphate percentage from 30 to 32%, alginate and derivatives thereof, for example alginate M with a main proportion of mannuronic acid and alginate G with a main proportion of guluronic acid, pectin and derivatives thereof, for example pectin with a esterification degree from 34 to 65%, fibrin and derivatives thereof, homo- and copolymers of acrylic acid crosslinked with a polyalkenyl polyether, or mixtures thereof.

More preferably, the gelling agent is selected from the group consisting of alginate, pectin and fibrin or mixtures thereof.

A derivative of alginate includes salts of alginate such as sodium alginate. Preferably, the alginate is a 1% alginate having a viscosity from 20 to 1000 cP, such as commercially available Keltone® ou Satialgine®.

The pectin derivative are preferably the commercially available CU 701 and CU-L 021/15.

Preferred mixtures of gelling agents include a mixture of alginate and pectin. In one embodiment, the gelling agent is alginate and/or pectin.

The compositions of the present application generally comprise from 0.01 wt % to 10 wt %, preferably from 0.01 wt % to 5 wt %, even more preferably from 0.05 wt % to 3 wt %, even more preferably from 0.1 wt % to 2 wt %, of the gelling agent relative to the total weight of the composition.

In a particular embodiment, the gelling composition comprises:
  15 wt % to 21 wt %, preferably 17 wt % to 19 wt %, of Poloxamer P407
  0 wt % to 5 wt %, preferably 1 wt % to 3 wt %, of Poloxamer P188
  0.01 wt % to 5 wt %, preferably 0.1 wt % to 2 wt %, of gelling agent such as sodium alginate,
based on the total weight of the composition.

In a preferred embodiment, the anticancer agent is selected from the group consisting of 5-FU (fluorouracile), oxaliplatin, cisplatin, folinic acid, irinotecan, metformin, paclitaxel, topotecan, etoposide, ifosfamide, altretamine, doxorubicine, tamoxifene, tamoxifene citrate, gemcitabine and mixtures thereof, in particular a mixture of 5-FU and cis-platin, a mixture of 5-FU and oxaliplatin, a mixture of 5-FU and folinic acid, a mixture of 5-FU, folinic acid and oxaliplatin, a mixture of oxaliplatin and paclitaxel or a mixture of cisplatin and paclitaxel. In the case of colorectal cancer, 5-FU is particularly preferred.

The compositions of the invention generally comprise from 0.1 wt % to 10 wt %, preferably from 0.25 wt % to 5 wt %, more preferably from 0.5 wt % to 2.5 wt % of anticancer agent based on the total weight of the composition.

The gelling compositions according to the invention may further comprise pharmaceutically acceptable additives such as rheofluidizing agent, excipients, stabilizers, preservatives, advantageously in an amount of 0.01 wt % to 5 wt % of pharmaceutically acceptable additive based on the total weight of the composition. As understood herein, a rheofluidizing agent reduces the fluidity of the composition when subjected to a shear stress. Examples of rheofluidizing agents include colloidal silica, such as aerosil, chitosans, carraghenans, alginates and pectins (in particular low esterified pectins such as pectins with a esterification degree of 34%). In this particular embodiment, the compositions of the invention typically comprise from 0.1 wt % to 1 wt % of rheofluidizing agent based on the total weight of the composition.

Pharmaceutically acceptable excipients include propylene glycol or salts such as sodium chloride, or of bioadhesive agents such as hydroxypropyl methylcellulose, methylcellulose or cross-linked acrylic acid polymers. In particular, the gelling composition of the invention further comprises sodium chloride, in particular 0 to 1% by weight of sodium chloride based on the total weight of the composition.

Examples of stabilizers are surfactants, polymers, polyols, a poloxamer, albumin, gelatin, trehalose, proteins, sugars, polyvinylpyrrolidone, N-acetyl-tryptophan ("NAT")), caprylate (i.e. sodium caprylate), a polysorbate (i.e. P80), amino acids, and divalent metal cations such as zinc.

The preservative is preferably selected from benzyl alcohol, cresols, benzoic acid, phenol, parabens and sorbic acid.

More preferably, the acceptable additive is a rheofluidizing agent such as colloidal silica.

In a particular embodiment, the gelling composition comprises:
  15 wt % to 21 wt %, preferably 17 wt % to 21 wt %, of Poloxamer P407;
  0 wt % to 5 wt %, preferably 1 wt % to 3 wt %, of Poloxamer P188;
  0.01 wt % to 5 wt %, preferably 0.1 wt % to 2 wt %, of a gelling agent such as sodium alginate;
  0.1 wt % to 0.4 wt % of pectins; or
  0.1 wt % to 0.4 wt % of pectins and 0.8 wt % to 1.6 wt % of aerosol; or
  0.1 wt % to 0.4 wt % of pectins and 0.1 wt % to 0.5 wt % of chitosan; and
  0.1 wt % to 10 wt %, preferably 0.25 wt % to 5 wt %, of the anticancer agent, preferably 5-FU;
based on the total weight of the composition, the remainder being water, in particular sterile water such as ultrapure water or water for injection.

The compositions of the invention may further comprise, in addition to the first anticancer agent, at least another therapeutic agent, in particular another anticancer agent, an antivascular agent or an antiangiogenic agent.

Examples of antivascular agent include vascular disruptive agents such as combretastatine and analogues, ombrabuline, fosbretabulin, plinabulin, lexibulin, crinobulin, flavones and flavone prodrugs, xanthone, vadimezan, mitoflaxone. Preferably, the antivascular agent is selected from combretastatine and analogues.

Examples of antiangiogenic agent include AntiVEGF such as bevacizumab, rmucizumab, and antiVEGF receptor such as ralmucizumab, sunitinib. Preferably, the antiangiogenic agent is selected from bevacizumab which can be associated to 5-fluorouracil.

Preferably, the other therapeutic agent is a second anticancer agent, which is advantageously different from the first anticancer agent of the composition, in particular selected from the group consisting of 5-FU (fluorouracile), oxaliplatin, cisplatin, folinic acid, irinotecan, metformin, paclitaxel, topotecan, etoposide, ifosfamide, altretamine, tamoxifene, tamoxifene citrate and mixtures thereof, in particular a mixture of 5-FU and cis-platin, a mixture of 5-FU and oxaliplatin, a mixture of 5-FU and folinic acid, a mixture of 5-FU, folinic acid and oxaliplatin, a mixture of oxaliplatin and paclitaxel or a mixture of cisplatin and paclitaxel. In the case of colorectal cancer, 5-FU is particularly preferred. More preferably, the second anticancer agent is in particular selected from the group consisting of 5-FU (fluorouracile), oxaliplatin, cisplatin, folinic acid, irinotecan, metformin, paclitaxel and mixtures thereof.

Advantageously, the gelling compositions according to the invention are sterile. In a particular embodiment, the gelling composition is in the form of a solution, which can be prepared and/or stored under sterile conditions in a vial, with a suitable sprayer or in a kit comprising a syringe.

Preferably, the gelling composition according to the present application is sprayed or spread on or injected into the application area, and instantly forms a gel on or within the application area.

Therefore, advantageously, the composition is preferably suitable for topical application or for injection, and may be in the form of a spray or a spreadable composition (for topical administration), or in the form of an injectable solution. In both cases, the composition may be initially (i.e. before application) liquid, and forms a gel when applied on the body through warming to body temperature.

According to another aspect, the invention relates to a solid composition for extemporaneous formation of a gelling composition of the invention, comprising:
  at least a poloxamer or mixture of poloxamers;
  at least a gelling agent;
  at least an anticancer agent; and
  more than 5 wt % of water.

The solid composition of the invention, when mixed with a suitable amount of an aqueous solution, leads to the extemporaneous formation of a gelling composition of the invention. Said aqueous solution is preferably saline or sterile water (such as ultrapure water or water for injection).

Typically, the gelling composition of the invention comprises more than 5 wt % water, even more preferably more than 10 wt % water, even more preferably between 15 wt % and 70 wt % of water.

The poloxamer, gelling agent, anticancer agent and optional additives are preferably as described above with regard to the gelling compositions of the invention, in particular as to their nature. Any combinations of preferred and particular embodiments of the poloxamer, gelling agent, anticancer agent and optional additives are encompassed in the solid composition of the invention. However, the weight ratios of the different constituents in the solid compositions are adapted so as to obtain the required weight ratios in the gelling composition once reconstituted.

The solid composition of the invention is preferably prepared by lyophilisation or by vacuum-drying of the corresponding gelling composition of the invention, or by vacuum-drying.

Alternatively, the invention relates to a two-component system for extemporaneous formation of a gelling composition of the invention, comprising:
  1) a first compartment comprising a solid composition comprising:
    at least a poloxamer or mixture of poloxamers;
    more than 5 wt % water; and
    at least a gelling agent and/or at least an anticancer agent; and
  2) a second compartment comprising an aqueous solution, preferably saline or sterile water (such as ultrapure water or water for injection), and optionally at least a gelling agent and/or at least an anticancer agent.

Typically, the gelling composition of the invention comprises more than 5 wt % water, even more preferably more than 10 wt % water, even more preferably between 15 wt % and 70 wt % of water. Said water is preferably sterile water (such as ultra pure water or water for injection).

Preferably, when the first compartment does not comprise a gelling agent, said gelling agent is in the aqueous solution of the second compartment. When the first compartment does not comprise an anticancer agent, said anticancer agent is in the aqueous solution of the second compartment. Advantageously, when the first compartment comprises both a gelling agent and an anticancer agent, the second compartment comprises an aqueous solution of gelling agent and anticancer agent.

In any case, the solid composition of the first compartment, when mixed with the aqueous solution of the second compartment, leads to the extemporaneous formation of a gelling composition of the invention.

The poloxamer, gelling agent, anticancer agent and optional additives are preferably as described above with regard to the gelling compositions of the invention, in particular as to their nature. Any combinations of preferred and particular embodiments of the poloxamer, gelling agent, anticancer agent and optional additives are encompassed in the solid composition of the invention. However, the weight ratios of the different constituents in the solid compositions are adapted so as to obtain the required weight ratios in the gelling composition once reconstituted.

According to another aspect, the present invention relates to a kit comprising at least:
  a first composition comprising the gelling composition of the invention, and
  a second composition comprising at least another therapeutic agent, in particular another anticancer agent, an antivascular agent or an antiangiogenic agent, preferably the other therapeutic agent is a second anticancer agent, such as 5-FU, oxaliplatin, cisplatin, folinic acid, irinotecan, metformine, paclitaxel and mixtures thereof,
for simultaneous, staggered or sequential use.

In particular, the second anticancer agent may be a mixture of 5-FU and cis-platin, a mixture of 5-FU and oxaliplatin, a mixture of 5-FU and folinic acid, a mixture of 5-FU, folinic acid and oxaliplatin, a mixture of oxaliplatin and paclitaxel or a mixture of cisplatin and paclitaxel. In the case of colorectal cancer, 5-FU is particularly preferred.

The one of skill in the art will of course select the second composition comprising another therapeutic agent, in particular the second anticancer agent taking into account the nature and stage of the tumour or cancer to be treated, as well as the age, sex, weight and sensitivity of the patient to be treated.

The kit of the invention may be used alone or in combination, simultaneously, separately or sequentially, with ionizing or non-ionizing radiations or hyperthermia.

The present invention also relates to the compositions or kits as described above, for use as a medicament, in particular for the treatment of cancer, preferably a cancer of a wall of the digestive system or a gynaecologic cancer.

In one embodiment, the cancer is a cancer of a wall of the digestive system, such as colorectal cancer, oesophagus cancer, or stomach cancer, preferably colorectal cancer.

In another embodiment, the cancer is a gynaecologic cancer, in particular ovarian or cervix cancer.

In a preferred embodiment, the cancer is a colorectal cancer or cervix cancer.

The compositions of the present invention are particularly well suited for use for treating colorectal cancer.

In a particular embodiment, the compositions or kits of the invention are used for size-reduction of a tumour before surgical removal of said tumour.

In another particular embodiment, the compositions or kits of the invention are used for preventing tumour recurrence after surgical removal (resection) of a tumour.

Preferably, the gelling compositions of the invention are locally administered.

In particular, administration of the gelling compositions of the invention by spraying or spreading provides uniform coverage of the area to be treated. When the gelling composition is in the form of a spray or of a solution to be spread, it is preferably used during surgery, after resection of the tumour, and is administered at the resection area.

When sprayed or spread at the tumour resection site, the penetration depth of the therapeutic agents from the gelling compositions of the invention is high due to the lack of high interstitial tumour pressure. This allows for a more limited resection of diseased parenchyma, thus maximizing the amount of functional tissues left behind, thus providing an alternative treatment greatly improving the life comfort of the patients, who, in the case of colorectal cancer, might have to undergo a colorectomy instead.

Administration by injection (advantageously intraperitoneal, intra-arterial or intravenous injection) is preferably used for size-reduction of a tumour before surgical removal of said tumour.

For size-reduction of a tumour before surgical removal of said tumour, topical application may also be envisaged when the tumour is situated in parts of the body which are easily accessible without the need to use injections, such as a tumour of the rectum or in the colon. In this case, the composition may be topically applied, for instance manually or through to apparatuses such as endoscopes or colonoscopes.

In another particular embodiment, the compositions or kits of the invention are used for preventing tumour recurrence after surgical removal of a tumour and/or treating small tumour.

In a particularly preferred embodiment, the compositions or kits of the invention are used for preventing tumour recurrence after surgical removal (resection) of a colorectal tumour, and/or for treating small colorectal tumours. The small tumours are, in particular not visible by the surgeon during resection, even with the use of intraoperative imaging.

According to another aspect, the present invention also relates to a method of treating the above cancers, which comprises administering to a patient in need thereof, an effective dose of a composition of the invention, preferably by local administration, in particular via parenteral or topical route (for instance or by spreading the compositions onto the site of resection) during surgery. The effective dose of a composition of the invention depends on many parameters such as, for example, the route of administration, weight, age, sex, status of the pathology treated and the sensitivity of the individual to be treated.

In another aspect, the present invention relates to a combination therapy comprising administering to a patient in need thereof a composition or kit of the invention, for simultaneous, staggered or sequential use with a treatment by radiotherapy or surgery.

The present invention also relates to a method for manufacturing a gelling composition of the invention, comprising the steps of:
- a) preparing a first poloxamer solution using the cold method;
- b) preparing a second solution containing an aqueous mixture of gelling agent and optionally additives;
- c) mixing the solutions obtained in step a) and b) at a temperature of between 15° C. and 25° C., preferably 20° C.;
- d) adding the anticancer agent to the mixed solution obtained in step c) and stirring until a clear solution is obtained;
- e) homogenizing the obtained clear solution;
- f) optionally adjusting the volume of the clear solution obtained in step e) to a predetermined final volume by adding water (preferably sterile).
- g) optionally sterilizing the solution.

The poloxamer, gelling agent, anticancer agent and optional additives are preferably as described above with regard to the gelling compositions of the invention, in particular as to their nature or ratio in the composition. Any combinations of preferred and particular embodiments of the poloxamer, gelling agent, anticancer agent and optional additives are encompassed in the method of the invention.

According to the present invention, the cold method comprises or consists of the following successive steps:
- a1) slowly adding the poloxamer or mixture of poloxamers to a predetermined volume of water (preferably sterile water (in particular ultrapure water or water for injection) to obtain a turbid poloxamer solution;
- a2) allowing the obtained turbid poloxamer solution to stand at a temperature of between 0 and 5° C., preferably 4° C., until the solution becomes clear;
- a3) homogenizing the obtained clear poloxamer solution;
- a4) optionally adjusting the volume of the obtained clear poloxamer solution to a predetermined final volume by adding water (preferably sterile).

Preferably, step a) of the method for manufacturing the gelling composition of the invention comprises steps a1) to a4).

Preferably, step b) of the method for manufacturing the gelling composition of the invention or consists of the following successive steps:
- b1) dispersing the gelling agent, and optionally additives, in water (preferably sterile water)
- b2) stirring until complete dissolution;
- b3) optionally heating the solution obtained in step b) to a temperature of between 15° C. and 25° C., preferably 20° C.

Step b2) may be carried out under heating so as to accelerate dissolution of the gelling agent and optional additives. For instance, step b2) may be carried out at a temperature of between 60° C. and 90° C., preferably 80° C.

The sterilization step g) may be carried out by sterilizing filtration or by radiation sterilization. In a particular embodiment, all the steps (that is to says steps a), b), c), d), e) and optional step f)) are carried out aseptically, so that the solution obtained at the end of step e) or f) is sterile; In this embodiment, no sterilization step g) is required.

The present invention also relates to a method for extemporaneously preparing the gelling composition of the invention, comprising the step of mixing the solid composition of the invention with a suitable amount of an aqueous solution, preferably saline or sterile water (such as ultrapure water or water for injection).

DESCRIPTION OF THE FIGURES

FIG. 13A represents a picture of the cells after 24 h of incubation with respectively the cell culture medium (1), a control hydrogel P407/P188/alginate 20/2/1 (2), a 5-FU hydrogel P407/P188/alginate/20/2/1.0.5 (3), an oxaliplatine hydrogel P407/P188/alginate/OX 20/2/1.0.3 (4) and a 5-FU oxaliplatine hydrogel P407/P188/alginate/5 FU/OX 20/2/1.0.5/0.3 (5). FIG. 13B represents the cytotoxicity of the different hydrogels containing 5-FU, oxaliplatin or the combinaison 5-FU, oxaliplatin after 24 h of incubation on A2780 ovarian cell lines. The viability was evaluated by MU test (MU cell proliferation assay, using 3(4,5-dimethylthiazolyl-2)-2,5-diphenyl tetrazolium bromide as known in the art) i.e. and estimate in percent of absorbance of the control wells.

FIG. 14A represents the volume of tumour growth overtime from day 4 to day 18 post implantation of the tumour in the mouse. The mouse receives a local treatment (intraperitoneal injection of 200 μl of gel) at day 6 using a composition of the invention comprising P407/P188/alginate/5 FU/OX (20/2/1.0.5/0.3) as the anticancer agent, or a control gel comprising P407/P188/alginate (20/2/1/0/0) and no therapeutic agent. The horizontal axis represents the time in days, while the vertical axis represents the intensity of the luminescence in photons/steradian/seconds/cm$^2$ after intraperitoneal injection of luciferin (median n=5). FIG. 14B represents a picture of the intestine after sacrifice at day 18 of the mouse who received a local treatment at day 6 using a composition of the invention comprising P407/P188/alginate/5 FU/OX (20/2/

Figure 1:
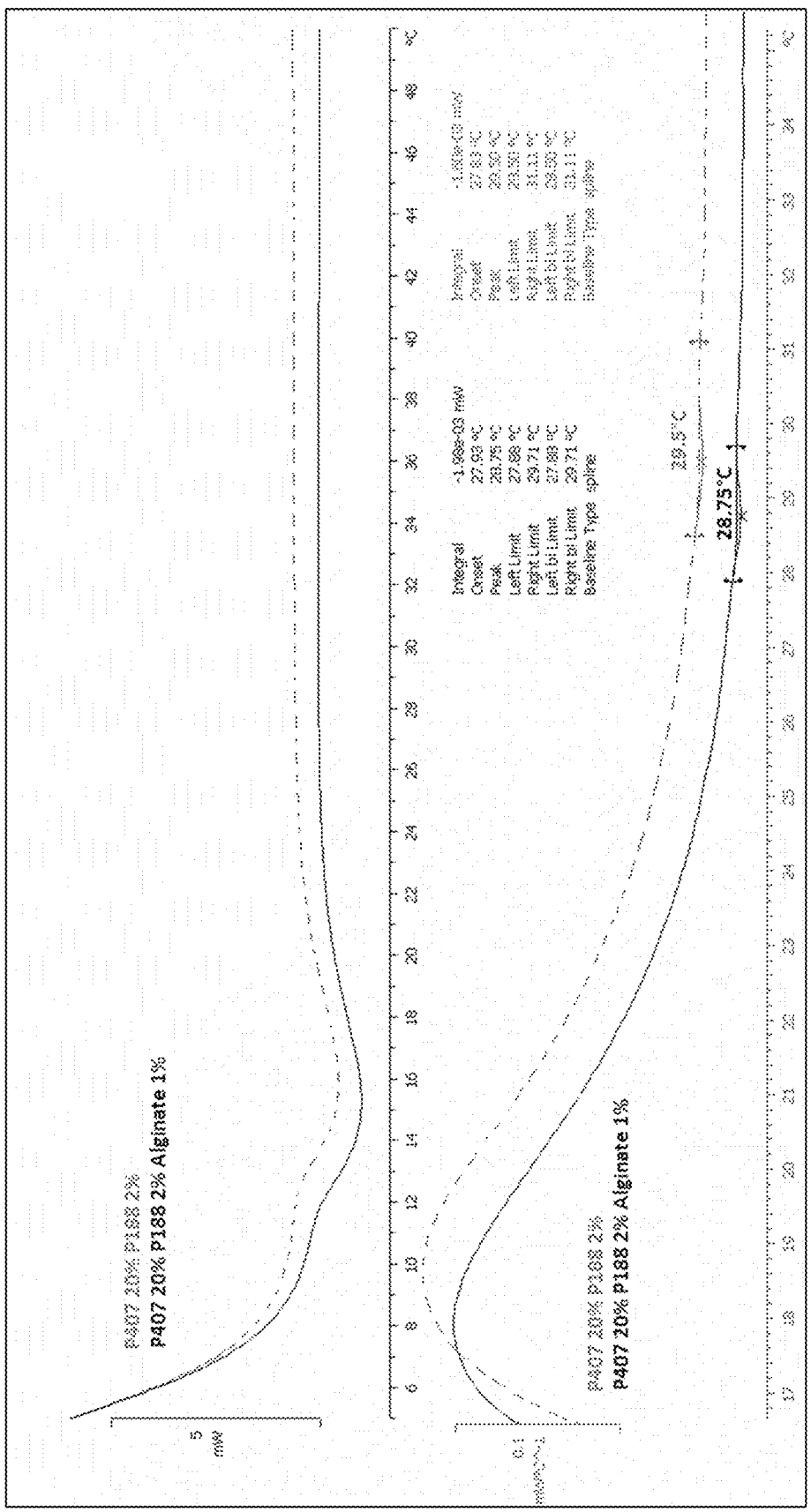
FIG. 1 represents the influence of the addition of 1% alginate in thermogels of the invention containing P407/P188 (20/2) on the micellisation and gelation temperature obtained by differential scanning calorimetry (Mettler Toledo, SSC7) using the following program: equilibrium at 5° C. during 10 minutes, then 5 to 40° C. at 5° C./minutes.

1.0.5/0.3) as the anticancer agent (4B 1), or a control gel comprising P407/P188/alginate (20/2/1/0/0) and no therapeutic agent (4B 2).

EXAMPLES

The following examples are meant to illustrate the present invention, but do not intend to limit its scope in any way.

Example 1

I. Material and Methods

1. Preparation of the Thermogel

The necessary amounts of poloxamer 407 and poloxamer 188 (P188) were mixed with approximately two thirds of the targeted final solution volume of water (Millipore, 0.22 [im, Resistivity=18.3 MH/cm) in a glass beaker. The solutions were stirred, while lying in an ice bath, during several hours with help of a magnetic stirrer and then left overnight at 4° C. Usually the mixture was dissolved in the upcoming day and the volume was adjusted with water to the exact desired volume (with the help of a graduated cylinder). Desired amounts of Alginate (Manucol D H, FMC BioPolymer, 9005-38-3) or pectin (Herbstreith&Fox) or chitosan (TM3728, Primex) or sataxiane or/and anticancer agent 5-FU were then added to the stock solution. The gelling composition was mixed until all components were dissolved and subsequently stored at 4° C.

Gel composition will be expressed in the following experimental section as: (w/v) % poloxamer 407/(w/v) % poloxamer 188/(w/v) % Alginate/(w/v) (or sataxiane, or pectin) % Anticancer Agent (5-FU).

2. Measurement of Gelation Temperature

The gelation temperature ($T_{gel}$) was determined by Differential Scanning calorimetry (DSC) and rheology.

By DSC: between 20-35 mg of the solution were sealed in aluminium pans and placed into the DSC instrument (DSC 1, Mettler Toledo). An empty aluminium pan (size: 40 µL) served as a reference sample. The instrument was equilibrated at 5° C. for 7 min prior to initiation of the scans. The sample was then heated to 40° C. at a heating rate of 5° C./min. Data analysis was performed with the software preinstalled in the instrument (STARe Software). The gelation temperature was determined as the small enthalpy change which was visible around at 10-12° C. above the big endothermic peak caused by micellization of the poloxamers, as already done in other studies (Nie et al, *Int. J. Nanomedicine*. 6 (2011) 151-166. doi:10.2147/IJN.S15057).

By rheology: a deformation was applied and varied between 0.01 to 100% at a fixed frequency of 1 Hz with a cone/plan mobile with an angle of 1°, a diameter of 50 mm and with a gap of 0.1 mm. The sample was left at room temperature for 1 hour, then approximately 750 µL was loaded on the pelletier plan which is submitted to a temperature increase. The viscoelastic moduli G' and G" are measured. The gelation temperature corresponds to the curve intersections.

3. In Vitro Cytotoxicity Tests 3.1 Cell Culture

CT26 cell line (American Type Culture Collection (ATCC, CRL-2638, LGC Standards, Molsheim, France) were used for the in vitro experiments. CT26 cells were originally obtained from an undifferentiated colon carcinoma chemically induced by N-nitroso-N-methylurethan [94] that was later cloned to obtain the stable CT26 cell line. This cell line was used for in vitro and in vivo evaluation.

For the evaluation of cytotoxicity we also used other type of cancer cell (B16 F0 mouse skin melanoma (ATCC® CRL-6322™), BWTG3: mouse hepatoma cell line, 3 LL (ATCC® CRL-1642™): mouse Lewis lung carcinoma) and test one cell line who as usually considered in the literature as non-cancerous cell (NIH 3T3 mouse fibroblast (ATCC® CRL-1658™)).

All of these tumour cell were cultured at 37° C. in a 5% $CO_2$-humidified atmosphere in Dulbecco's Modified Eagle Medium (DMEM, Gibco) containing 10% fetal bovine serum (FBS, Gibco Life technologies), 100 µM of streptomycin, and 100 U/mL of penicillin. If not mentioned otherwise, this mix will be simplified as cell culture medium.

The mouse fibroblast cell were cultured in the same condition but need a culture medium with Dulbecco's Modified Eagle Medium (DMEM, Gibco) containing 10% bovine serum (Calf serum, Gibco Life technologies), 100 µM of streptomycin, and 100 U/mL of penicillin 3.2 Cytotoxicity Evaluation In a 24-well plate (TPP Techno Plastic Products, 92024) 200 000 cell/mL (0.1 mL culture medium/per well) were cultured overnight in the incubator (37° C.). The next day the medium was removed and 300 µl of gel was deposed onto cells. The number of viable cells was determined by the 3-(4,5-Dimethylthiazol-2-yl)-2,5-diphenyltetrazolium bromide (MTT, Sigma Aldrich, 298-93-1) colorimetric assay. After 6 h of incubation, 100 µL of the MTT solution (4 mg/mL MTT in cell culture medium) was added to the cells. The solution was removed and replaced by 100 µL of DMSO and the plate was shaken during 10 min. The absorption was subsequently measured at 562 nm.

In a 96-well plate (TPP Techno Plastic Products, 92024) 200 000 cell/mL (0.1 mL culture medium/per well) were cultured overnight in the incubator (37° C.). The next day the medium was removed and different amount of a thermogel of the invention (P407/Sataxiane/5 FU) was deposed onto cells. The number of viable cells was determined by the 3-(4,5-Dimethylthiazol-2-yl)-2,5-diphenyltetrazolium bromide (MTT, Sigma Aldrich, 298-93-1) colorimetric assay. After 72 h of incubation, 100 µL of the MTT solution (4 mg/mL MTT in cell culture medium) was added to the cells. The solution was removed and replaced by 100 µL of DMSO and the plate was shaken during 10 min. The absorption was subsequently measured at 562 nm.

4. In Vivo Anti-Tumour Activity 4.1 Mice

The experiments were carried out in Balb/CJRJ female mice (Janvier, St Genest de Lisle, France), aged from 6 to 7 weeks. Animal experiments were conducted according to European and national guidelines and were approved by the institutional ethics committee.

4.2 Tumor Implantation into Mice

As tumour model, a modified cell line of the CT26 cell line was used, the CT26_luc cell line. CT26_luc cells in culture medium were injected subcutaneously (ectopically) into the right and left flank of the mouse. 15 days after implantation a tumour bearing mouse was sacrificed, her tumour resected and placed into sterile PBS. The tumour is then cut into 20-30 $mm^3$ fragments and inserted with the help of a 12 gauge trocar (38 mm) subcutaneously into the right mouse flank previously disinfected with alcohol. The same was done on the left mouse flank.

4.3 Tumour Resection and Thermogel Insertion 14 days after tumour insertion the mice were anaesthetized (Ketamine 80 mg/kg, Xylazine 10 mg/kg 300 µL intraperitoneal) and the area around their 2 tumours was shaved and disinfected with alcohol. During the anaesthesia the mouse was kept at physiologic temperature. An incision of 1-2 cm was made in the proximity of the tumour and the tumour was subsequently resected without leaving macroscopic residuals. In the remaining cavity 100 μL of the hydrogel formulations P407/P188/Alginate/5 Fu 20/2/1.0.5 were inserted with the help of syringe. The wound was closed with silk thread 5.0.

4.4 Inhibition of Tumour Growth after Gel Injection 8 days after tumour insertion the mice were anaesthetized (Ketamine 80 mg/kg, Xylazine 10 mg/kg 300 μL intraperitoneal) and the area around their 2 tumours was shaved and disinfected with alcohol. At this time point 60 μl of thermogel of the invention P407/satiaxane/5 Fu 21.0.1.0.5 or the control thermogel without 5 FU was injected into the tumour.

4.4 Tumor Follow-Up

The size of the tumour was measured principally by optical imaging. The mice were therefore injected intraperitoneally 20 min before imaging with 2 mg luciferin (200 μl, 10 mg/ml) (D luciferin K salt, INTERCHIM). By reacting with luciferase a photon signal is produced which can be detected by the camera (PhotonIMAGER™ Biospace Lab). The mice were thus imaged during 10 min while being under anaesthesia with isoflurane. Image analysis was performed with the M3 Vision software developed by Biospace Lab.

Furthermore tumour volume was measured at some time points with the help of a calliper. The volume was estimated as follows: (length×width$^2$)/2.

This also allowed determining the time point for killing the mice: Mice were sacrificed as soon their tumour volume exceeded 1000 mm$^3$. Their tumour was subsequently resected and weighed.

II. Results

Figure 2:
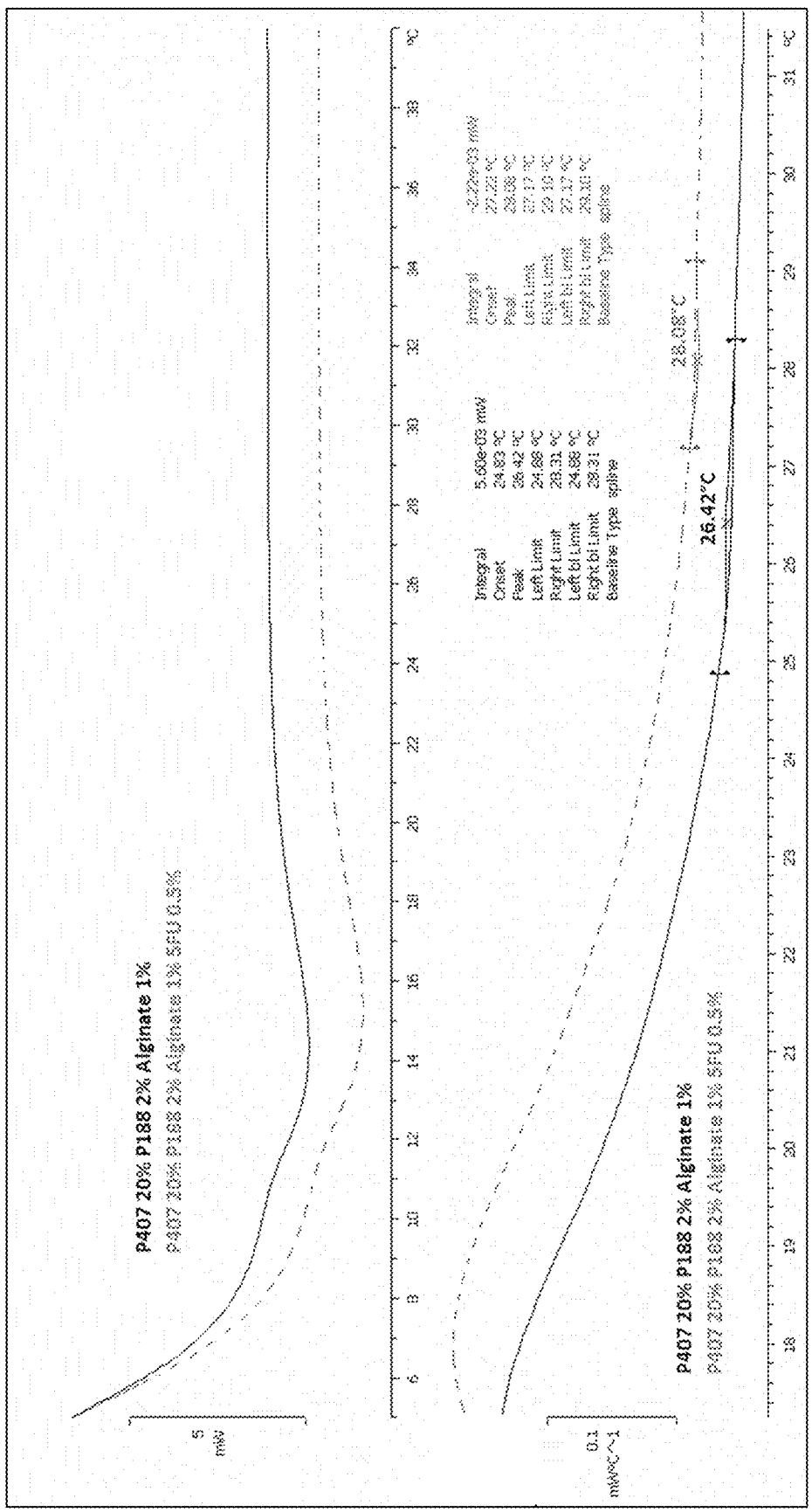
FIG. 2 represents the influence of the addition of 0.5% 5 FU in thermogels of the invention containing P407/P188/Alginate (20/2/1) on the micellization and gelation temperature of various gel composition obtained by differential scanning calorimetry (Mettler Toledo, SSC7) using the following program: equilibrium at 5° C. during 10 minutes, then 5 to 40° C. at 5° C./minutes.
Figure 3:
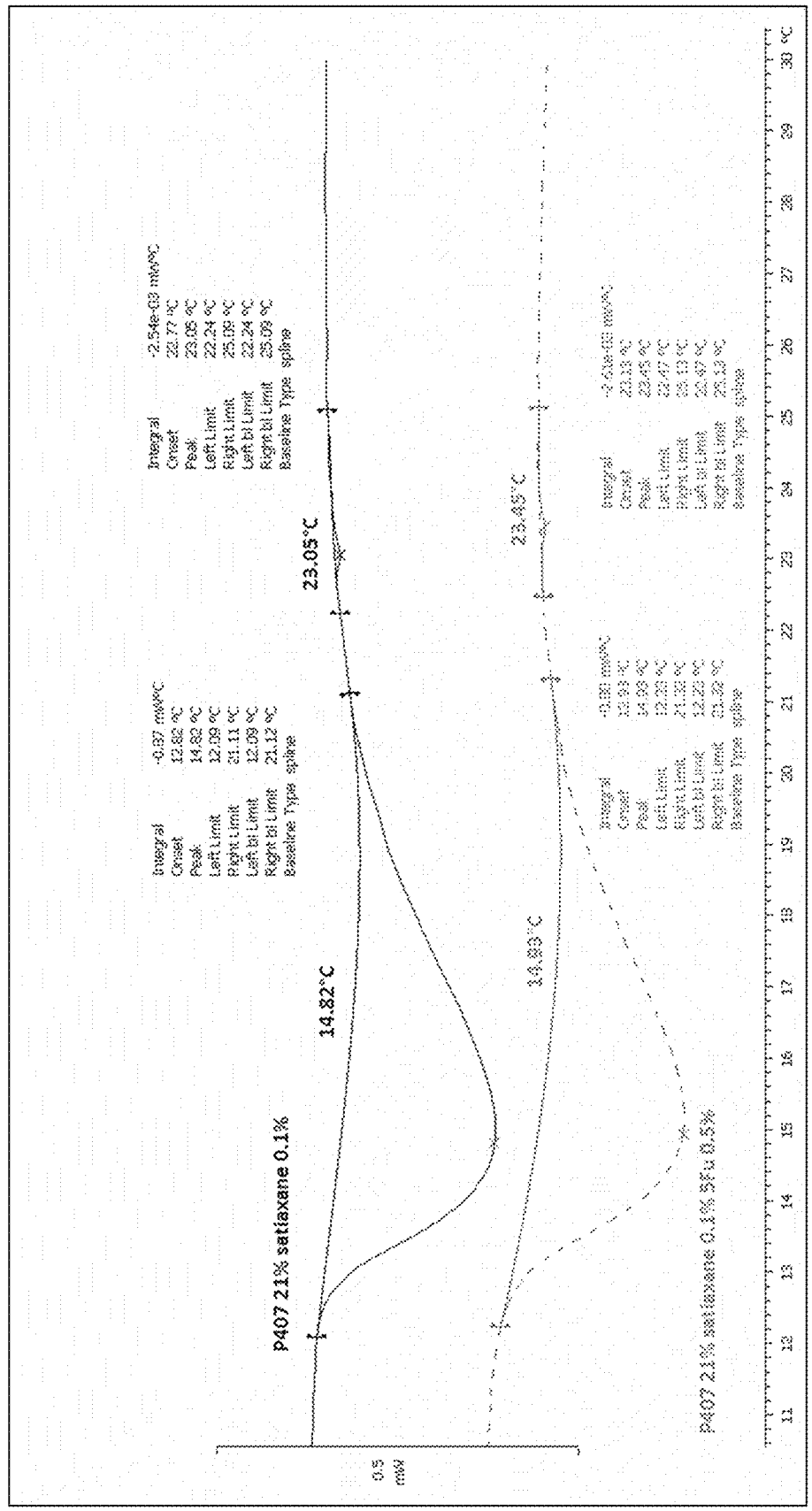
FIG. 3 represents the influence of the addition of 0.5% 5 FU in thermogels of the invention containing P407/P188/Alginate (20/2/1) on the micellization and gelation temperature of various gel composition obtained by differential scanning calorimetry (Mettler Toledo, SSC7) using the following program: equilibrium at 5° C. during 10 minutes, then 5 to 40° C. at 5° C./minutes.
Figure 4:
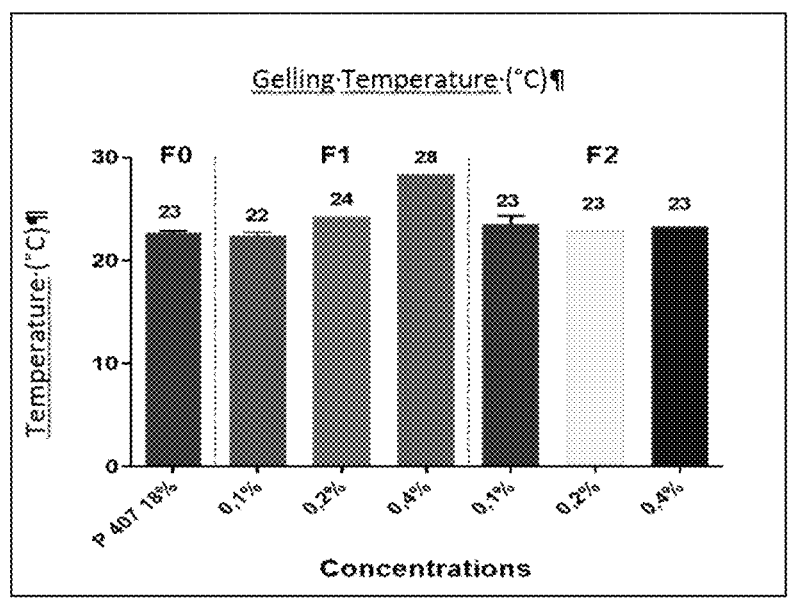
FIG. 4 represents the influence of the insertion of pectin in the gelation temperature of the gels containing 18 wt % P407. F1 represents a formulation containing the pectin 701 at various wt concentration. F2 represents a formulation containing the pectin CU-L at various wt concentration. FO does not contain pectin. Gelation temperatures were obtained by rheology studies.

Gels based on poloxamer and containing additive components to improve adhesion and/or strengths were obtained. As a first approach, the gelation temperatures obtained by DSC and rheology give the properties of the gels (FIGS. 1 and 2). Addition of 1% alginate in the formulation of P407/P188 lowered the gelation temperature by 1° to 2° C. As the objective of these gels is to be used for local delivery of cytotoxic agents, the cytotoxic 5-FU was embedded within the gel and tested for its maintained gelation (FIG. 2). It was found that addition of 0.5% 5-FU increased by 2° C. the gelation temperature. A similar result was obtained when 5 FU was embedded in the P407/Sataxiane 21.0.1 (FIG. 3). Another composition containing pectin was tested for its gelation ability. Addition of various percentages of pectin in a gel containing P407 was also shown to increase the temperature of gelation as obtained by rheology (FIG. 4).

Figure 5:
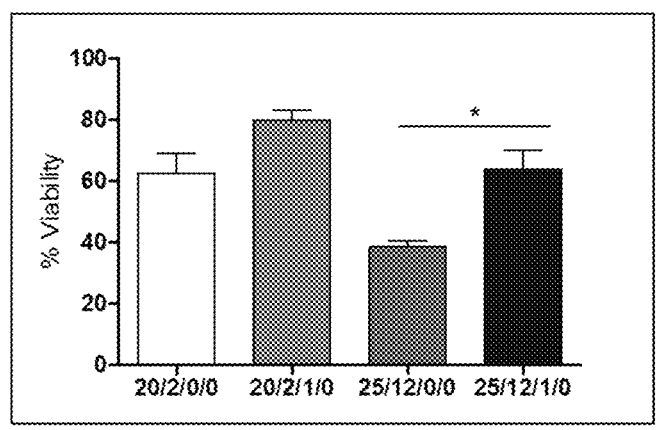
FIG. 5 represents the cytotoxicity of 300 μl of gels containing different amount of the invention component P407, P188 and alginate after 6 h of incubation on CT26 cell lines.
Figure 6:
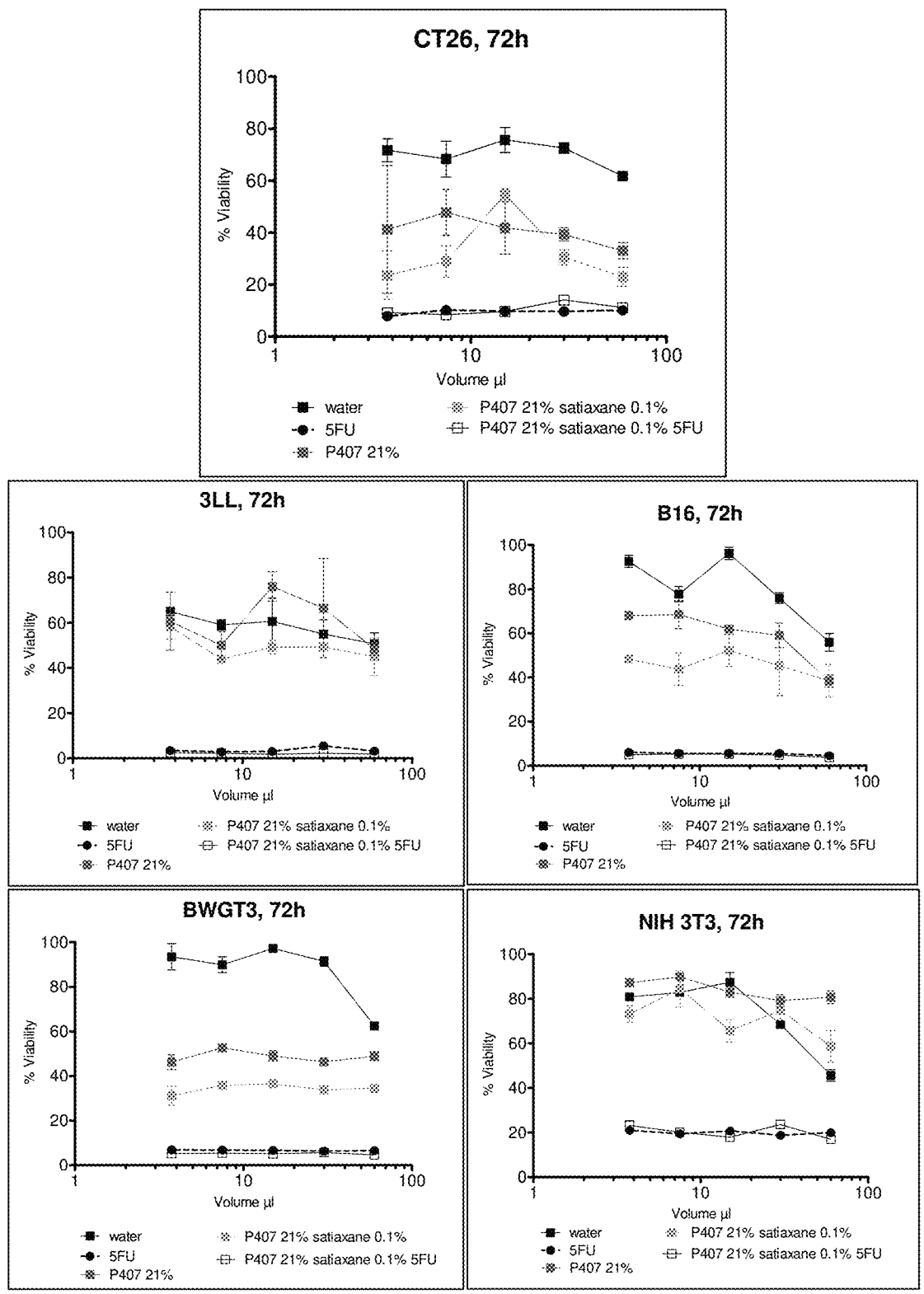
FIG. 6 represents the cytotoxicity of gels containing 5-FU on different cell lines using a composition of the invention comprising P407/Sataxiane/5-FU: 21 wt %/0.1% wt/0.5 wt %. These experiments were realized with various cell types: B16-F0 (ATCC® CRL-6322™): mouse skin melanoma, NIH 3T3 (ATCC® CRL-1658™): mouse fibroblast, BWTG3: mouse hepatoma cell line, 3 LL (ATCC® CRL-1642™): mouse Lewis lung carcinoma and CT26 (ATCC® CRL-2638™): mouse colon Carcinoma.

The maintained cytotoxic effect of 5-FU within the thermogel with a formulation of the invention P407/P188/Alginate was found on tumor colon CT26 (FIG. 5), and also with the mixture P407/Sataxiane (21.0.1.0.5) on various cell lines (FIG. 6). The cytotoxicity of the 5-FU derivative was maintained when embedded in the gel. Interestingly the thermogel was found to be more toxic onto cancer cell as compared to non cancer NIH 3T3 cells probably due to the slowest doubling time of fibroblast cell.

Figure 7:
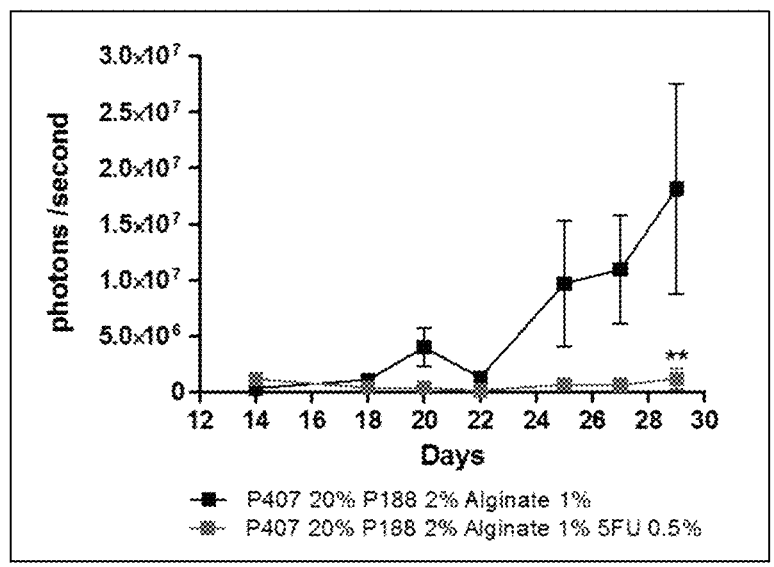
FIG. 7 represents the volume of tumour growth overtime showing the tumour recurrence in the mouse after resection of a CT26 luciferase positive tumour at day 14 and treatment using a composition of the invention comprising P407/P188/alginate/5-FU: 20 wt %/2 wt %/1 wt %/0.5 wt % as the anticancer agent, or a control gel comprising 20 wt % of P407, 2 wt % of P188, 1 wt % of alginate (20/2/1/0) and no therapeutic agent. The horizontal axis represents the time in days, while the vertical axis represents the intensity of the luminescence after intraperitoneal injection of luciferin in photons/seconds.
Figure 8:
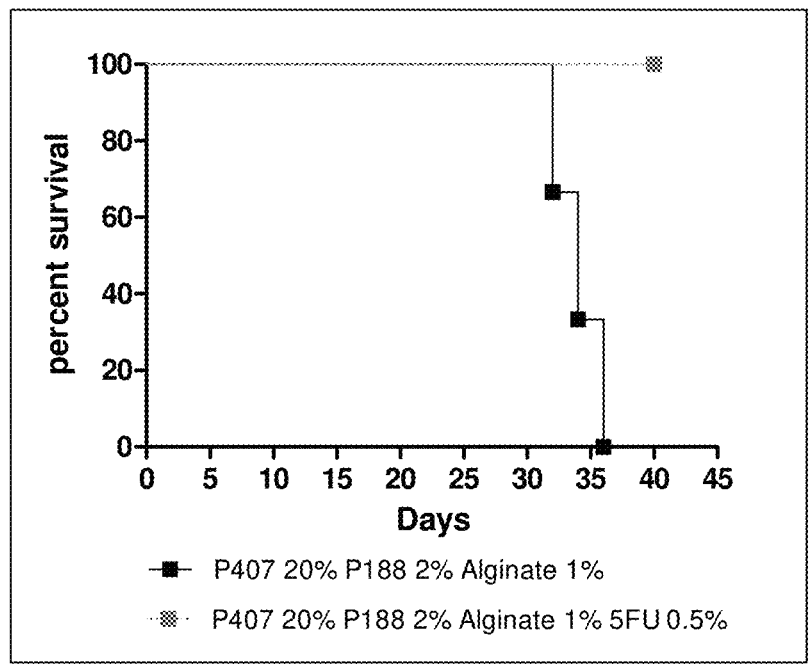
FIG. 8 represents the mice survival after resection of a CT26 tumour and local treatment with the thermogel using a composition of the invention comprising 20 wt % of P407, 2 wt % of P188, 1 wt % of alginate and 0.5 wt % 5-FU (20/2/1/0.5) as the anticancer agent, or a control gel comprising 20 wt % of P407, 2 wt % of P188, 1 wt % of alginate and no therapeutic agent (20/2/1/0). The horizontal axis represents the time in days, while the vertical axis represents the percentage of mice survival. The drop out reflects the death of the mice.

In vivo experiments were carried out on luciferase positive Colon CT26 xenografted in the flank of BalBC mice. Two different experiments were performed. First, the tumour was removed after Day 11 and the mice locally treated in the area of the resection with a thermogel of the invention. Second, the tumour was left and a thermogel of the invention directly injected within the tumour 11 days after implantation. The local treatment after resection with a gel containing P407/P188/Alginate/5 FU (20/2/1.0.5) showed a significative tumour growth delay 15 days post treatment as compared to the gel which did not contain any cytotoxic (p<0.05) (FIG. 7). Moreover, mice survival was increased thanks to the local treatment as compared to untreated mice (FIG. 8).

Figure 9:
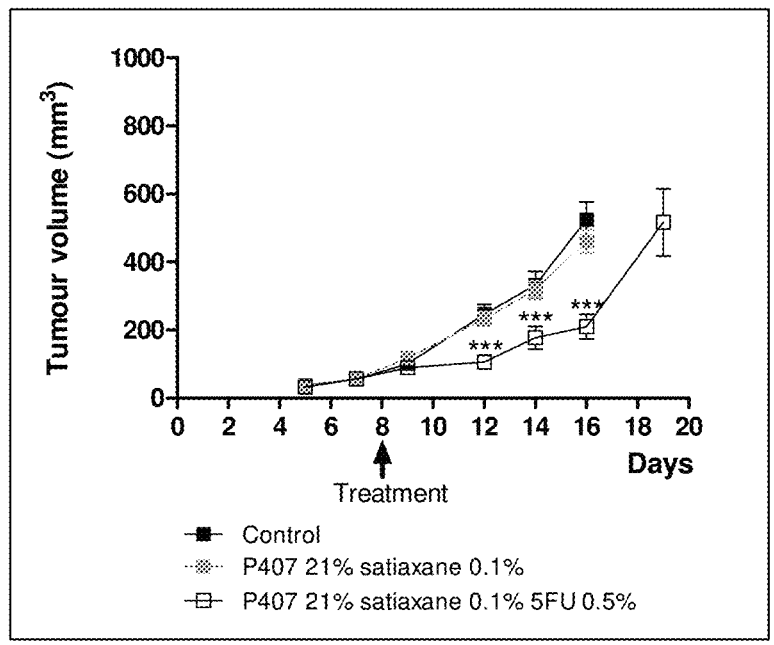
FIG. 9 represents the volume of tumour growth overtime from day 4 to day 20 post intratumoral injection of the thermogel. Mouse have a local treatment (intratumour injection of 60 μl of gel) at day 8 using a composition of the invention comprising 21 wt % of P407, 0.1% satiaxane and 0.5 wt % 5-FU as the anticancer agent, or a control gel comprising 21 wt % of P4070.1% satiaxane and no therapeutic agent. The horizontal axis represents the time in days, while the vertical axis represents the tumour volume in mm3 obtain after external measurement with the help of a calliper. Data were submitted to 2ways ANOVA with Bonferroni posttests statistical analyses.
Figure 10:
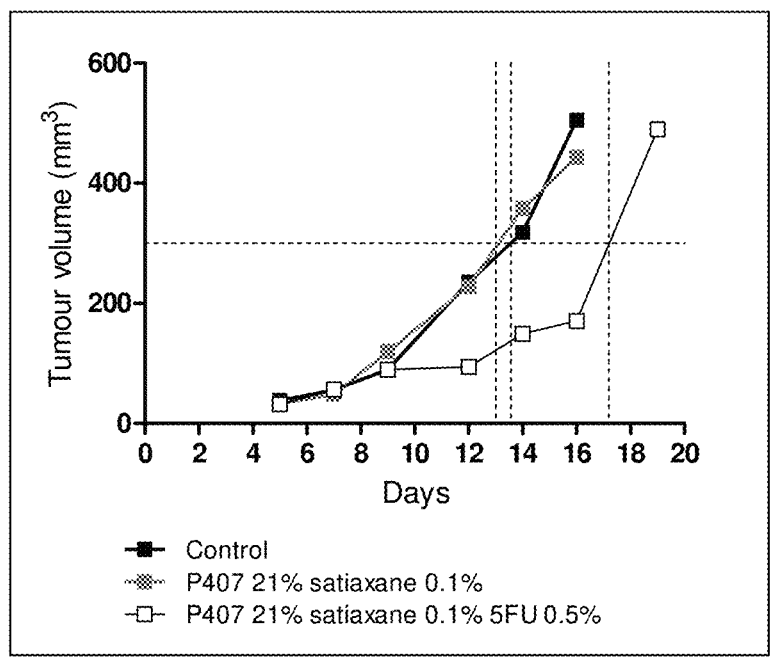
FIG. 10 represents the median tumour growth in the mouse after intratumoral injection of the thermogel using a composition of the invention comprising 21 wt % of P407, 0.1% satiaxane and 0.5 wt % 5-FU as the anticancer agent, or a control gel (Gel K) comprising 21 wt % of P407, 0.1% satiaxane and no therapeutic agent. The horizontal axis represents the time in days, while the vertical axis tumour volume in mm3. Data such as time delay, median size and the ratio is given in the table below the figure (Table 2). Compounds are considered active if this ratio is less than 42%.

The second treatment consisting in an intratumoral injection within the tumour showed even more enthousiastic results. The composition P407/sataxiane/5 FU (21.0.2/0.5) showed a reduced tumour growth as compared to the free gel or the untreated mice (FIG. 9). The median data gave a tumour delay of 4.2 days and a T/C of 33%. As T/C<42% is the minimal ratio for a compound to be considered active, we show here that 5 FU is active when initially administered in the gel, meaning that it diffuses through the gel to play its cytotoxic role (FIG. 10).

Figure 11:
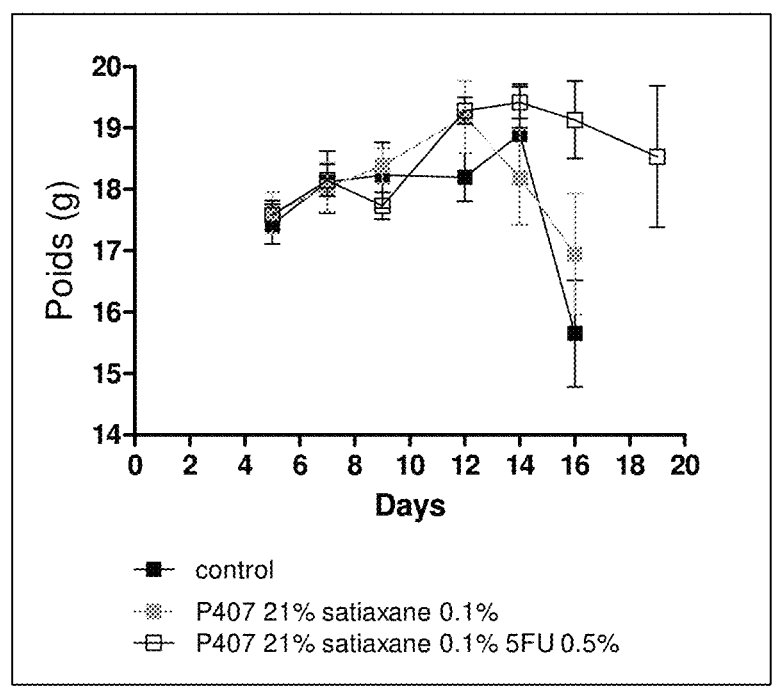
FIG. 11 represents the mice weight overtime from day 4 to day 20 post intratumoral injection of the thermogel.

More noticeable is the absence of systemic toxic effect that we could observe by following the weight loss of the animal. In opposite to the weight of the animals submitted to tumor growth, the local delivery of 5 FU is able to delay the tumor growth without inducing any systemic cytotoxicity (FIG. 11).

Example 2

I. Material and Methods

Materials

All the hydrogels were prepared using water for injection purposes from Lavoisier France (Paris, France). Kolliphor® P407 and Kolliphor® P188 of pharmaceutical use grade were obtained from BASF (France). Protanal® LF 10/60 FT (alginate) was obtained from FMC Biopolymer laboratories (Norway). Protasal® CL 113 (chitosan) was obtained from Novamatrix (Norway). Satiaxane® UCX930 (xanthan gum) was obtained from Cargill France (Saint-Germain-en-Laye, France). Carbopol® 971P NF and Carbopol® 974P NF (Lubrizol, France). Aerosil® A200 was obtained from Ageps laboratories (Paris, France).

Preparation of the Formulations

The hydrogel was prepared on a volume basis. Concentrations of all the components reported here are expressed as weight/volume percentage (% w/v). The poloxamer solutions were prepared using the cold method (Schmolka, 1972). P407 (17%-20%) combined with P188 (1%-2%-5%) were slowly added to a certain volume of water for injection purposes, and then, the preparations were left at 4° C. until clear solutions were obtained. The preparations were then gently homogenized with magnetic stirrers. A volume of water for injection purposes was then added to adjust the volume to the total amount.

For the preparation of the blend of poloxamer/Satiaxane, poloxamer/Alginate, poloxamer/Chitosan, the Satiaxane (0.05% and 0.1%), the Alginate (0.25%, 0.5% and 1%), and the Chitosan (0.25%, 0.5% and 1%) solutions were first prepared by dispersing the required amount in a certain volume of water for injections, stirring continuously until complete dissolution. Then, the required amount of P407 and P188 were added to the already swollen solutions. The preparations were gently homogenized with magnetic stirrers, until the adjustment volume as previously described.

The hydrogels made with Carbomers (0.2%) were prepared by dispersing the required amount of carbomers in a certain volume. Poloxamers were then added and dissolved until clear solutions were obtained. Then, the clear and homogeneous solutions were adjusted to a pH value between 5.0 and 5.5 by 1M sodium hydroxide, to get chemical stability.

Formulations for the blend of poloxamer/Aerosil (1% and 2%), required a preliminar dispersion of the aerosil powder in water for injections using an Ultra-Turrax, at 15000 rpm during at least 8 minutes of dispersion. A volume of aerosil dispersion was then slowly added to the swollen P407/P188 hydrogels, under magnetic stirring, at 4° C. The compositions of prepared formulations are shown in Table 1.

Thermal Analysis and Visco-Elastic Parameters of Poloxamer Formulations by Rheological Analyses (Table 1)

Table 1 provides gelation temperature and viscoelastic parameters of various mixtures of poloxamers (17/1 and 20/1) containing bioadhesive copolymers such as alginates, chitosans and carbopol at various percentages (0.05 to 1)

TABLE 1

Gelation temperatures and rheological measurements results for each formulation at 37° C.

| Composition | Ratio (% w/w) | Tg (° C.) | G" (Pa) | G' (Pa) | G"/G' | |
|---|---|---|---|---|---|---|
| P407/P188 | 17/1 | 29.0 ± 0.9 | 976 ± 135 | 6738 ± 185 | 0.14 ± 0.02 | |
| P407/P188/Alginate | 17/1/0.25 | 29.9 ± 1.3 | 143 ± 96 | 485 ± 24 | 0.29 ± 0.18 | |
| P407/P188/Alginate | 17/1/0.5 | 31 ± 0.7 | 433 ± 78.3 | 1082 ± 305 | 0.41 ± 0.04 | |
| P407/P188/Alginate | 17/1/1 | 28.9 ± 0.3 | 1033 ± 88 | 4665 ± 434 | 0.22 ± 0.01 | |
| P407/P188/Chitosan | 17/1/0.25 | 29.4 ± 0.3 | 833 ± 250 | 2712 ± 1345 | 0.34 ± 0.09 | G'max |
| P407/P188/Chitosan | 17/1/0.5 | 29.4 ± 0.4 | 934 ± 32 | 4177 ± 206. | 0.22 ± 0.01 | |
| P407/P188/Chitosan | 17/1/1 | 29.1 ± 0.4 | 849 ± 28 | 7811 ± 165 | 0.11 ± 0.00 | |
| P407/P188/Carbopol 974NF | 17/1/0.2 | 32.1 ± 0.7 | 41 ± 15 | 396 ± 201 | 0.11 ± 0.01 | |
| P407/P188/Carbopol 971NF | 17/1/0.2 | 39.9 ± 2.3 | 1.52 ± 0.17 | 0.63 ± 0.1 | 2.46 ± 0.26 | |
| P407/P188/Xanthan Gum | 17/1/0.05 | 29.0 ± 0.8 | 555 ± 3 | 1669 ± 11 | 0.33 ± 0.00 | |
| P407/P188/Xanthan Gum | 17/1/0.1 | 30.9 ± 0.4 | 650 ± 165 | 2700 ± 1046 | 0.25 ± 0.04 | |
| P407/P188/Aerosil | 17/1/1 | 30.0 ± 0.7 | 61 ± 26 | 601 ± 282 | 0.10 ± 0.00 | |
| P407/P188/Aerosil | 17/1/2 | 29.9 ± 0.7 | 491 ± 89 | 2149 ± 825 | 0.24 ± 0.04 | |
| P407/P188 | 20/2 | 26.5 ± 0.3 | 729 ± 28 | 15840 ± 191 | 0.05 ± 0.00 | |
| P407/P188/Alginate | 20/2/0.25 | 29.5 ± 1.7 | 709 ± 161 | 12588 ± 3647 | 0.06 ± 0.03 | |
| P407/P188/Alginate | 20/2/0.5 | 25.2 ± 0.6 | 455 ± 14 | 15715 ± 292 | 0.03 ± 0.00 | |
| P407/P188/Alginate | 20/2/1 | 26.6 ± 0.0 | 535 ± 66 | 14469 ± 756 | 0.04 ± 0.00 | |
| P407/P188/Chitosan | 20/2/0.25 | 27.7 ± 0.8 | 799 ± 36 | 13409 ± 88 | 0.06 ± 0.00 | |
| P407/P188/Chitosan | 20/2/0.5 | 26.9 ± 0.1 | 641 ± 79 | 14417 ± 186 | 0.05 ± 0.01 | |
| P407/P188/Chitosan | 20/2/1 | 26.9 ± 0.1 | 567. ± 41 | 14992 ± 155 | 0.04 ± 0.00 | |
| P407/P188/Carbopol 974NF | 20/2/0.2 | 29.0 ± 0.5 | 457 ± 4 | 11541 ± 291 | 0.04 ± 0.00 | |
| P407/P188/Carbopol 971NF | 20/2/0.2 | 31.0 ± 0.3 | 530 ± 66 | 5445 ± 709 | 0.10 ± 0.03 | |
| P407/P188/Xanthan Gum | 20/2/0.05 | 27.1 ± 0.1 | 822 ± 43 | 15957 ± 596 | 0.05 ± 0.00 | |
| P407/P188/Xanthan Gum | 20/2/0.1 | 26.3 ± 1 | 1003 ± 11 | 13743 ± 664 | 0.07 ± 0.00 | |
| P407/P188/Aerosil | 20/2/1 | 26.8 ± 0.2 | 399 ± 110 | 16160 ± 78 | 0.03 ± 0.01 | |
| P407/P188/Aerosil | 20/2/2 | 27.2 ± 0.5 | 554 ± 74 | 15423 ± 388 | 0.04 ± 0.00 | |
| P407/P188 | 20/5 | 30.3 ± 1 | 1022 ± 57 | 11316 ± 661 | 0.09 ± 0.00 | |
| P407/P188/Alginate | 20/5/0.25 | 34.3 ± 0.1 | 1040 ± 57 | 10419 ± 1395 | 0.1 ± 0.01 | |
| P407/P188/Alginate | 20/5/0.5 | 30.3 ± 1.1 | 765 ± 57 | 12146 ± 1395 | 0.06 ± 0.01 | |
| P407/P188/Alginate | 20/5/1 | 30.5 ± 1.1 | 740 ± 118 | 11881 ± 485 | 0.06 ± 0.01 | |
| P407/P188/Chitosan | 20/5/0.25 | 31.6 ± 0.2 | 1175 ± 230 | 9447 ± 1056 | 0.13 ± 0.04 | |
| P407/P188/Chitosan | 20/5/0.5 | 32.2 ± 0.4 | 968 ± 33 | 9568 ± 45 | 0.10 ± 0.00 | |
| P407/P188/Chitosan | 20/5/1 | 31.8 ± 0.5 | 1223 ± 59 | 6272 ± 1141 | 0.20 ± 0.02 | |
| P407/P188/Carbopol 974NF | 20/5/0.2 | 30.3 ± 0.2 | 539 ± 87 | 13226 ± 1688 | 0.04 ± 0.00 | |
| P407/P188/Carbopol 971NF | 20/5/0.2 | 32.0 ± 1.4 | 64 ± 22 | 812 ± 458 | 0.08 ± 0.02 | |
| P407/P188/Xanthan Gum | 20/5/0.05 | 29.7 ± 0.3 | 1211 ± 97 | 8667 ± 1992 | 0.14 ± 0.03 | |
| P407/P188/Xanthan Gum | 20/5/0.1 | 33.4 ± 1.4 | 592 ± 57 | 1697 ± 293 | 0.35 ± 0.04 | |
| P407/P188/Aerosil | 20/5/1 | 31.7 ± 0.7 | 1120 ± 15 | 5347 ± 385 | 0.21 ± 0.01 | |
| P407/P188/Aerosil | 20/5/2 | 33 ± 0.7 | 370 ± 206 | 1095 ± 401 | 0.33 ± 0.07 | |

Tg = Gelation Temperature − G" = Viscous Modulus − G' = Elastic Modulus − tanδ = G"/G = loss factor.

The rheological analysis was carried out using an Anton Paar MCR102 rheometer (France). The measuring system was a cone plate combination (diameter=50 mm; angle=1°). Non destructive oscillatory measurements at 1 Hz allow to obtain the elastic modulus (G'), the viscous modulus (G") and the phase angle (tan σ=G"/G'). The plate was heated at a rate of 1° C./min from 20° C. to 50° C. Firstly, the viscous modulus (G") is higher than the elastic modulus (G'). The sol-gel transition temperature was defined as the point where the two modulus intersect, to make the elastic modulus (G') higher than the viscous modulus (G"). All the measurements were carried out in triplicate and the results were expressed as mean±standard deviation.

Rheofluidification Test of Poloxamer Formulations by Rheological Analyses (Table 2)

In order to determine the shear thinning of aerosil in the various formulations, rheofluidification tests were carried out by measuring the viscosity η in mPa·s over a shear rate $\dot{\gamma}$ from 0.1 to 10000 $s^{-1}$, at 20° C. All the measurements were carried out in triplicate. Means and standard deviations were calculated, and reported to plot a linear calibration graph given by equation y=ax+b. The shear thinning was determined by comparing the slopes (a), and also by comparing the intercepts (b) which give the viscosity for each formulation.

TABLE 2

Shear Thinning of Aerosil ®200 effect determined by rheological measurements and viscosity (shear rate from 0 to 10 $s^{-1}$).

| Composition | Ratio (% w/w) | Viscosity (mPa · s) | Shear Thinning effect of aerosil (relative unit) |
|---|---|---|---|
| P407/P188 | 17/1 | 85.1 | 0.5 |
| P407/P188/Aerosil | 17/1/1 | 85.8 | 0.58 |
| P407/P188/Aerosil | 17/1/2 | 95.1 | 0.85 |
| P407/P188 | 20/2 | 122.0 | 0.68 |
| P407/P188/Aerosil | 20/2/1 | 141.4 | 0.87 |
| P407/P188/Aerosil | 20/2/2 | 156.5 | 1.4 |

Thermal Analysis and Energy of the Transition in Formulations Incorporating Drugs (Table 3)

The system DSC METTLER TOLEDO DSC 1 Star System was used for these experiments with aluminium crucibles of 40 µL. The sample was weighed in the crucible than loaded in the system. The program consisted in maintaining the sample at 5° C. during 5 minutes, proceed to 40° C. with a ramp of 1° C./min and repeat 3 to 6 times the experiment until the error of the mean data did not exceed 10%.

TABLE 3

Micellisation temperature (Tm) and enthalpy of the transition (mW) results for formulations incorporating drugs, either 5Fu, Oxaliplatin or a combination of both, as measured by differential scanning calorimetry

| P407/P188/alginate/5Fu/OxPt w/w/w | Tm (° C.) | Enthalpy mW |
|---|---|---|
| 17/1/1/0/0 | 15.5 | 0.28 |
| 17/1/1/0.5/0 | 15.6 | 0.56 |
| 17/1/1/0/0.1 | 15.3 | 0.33 |
| 17/1/1/0.5/0.1 | 14.7 | 0.37 |
| — | — | — |
| 20/2/1/0/0 | 14.5 | 1.2 |
| 20/2/1/0.5/0 | 14.3 | 1.4 |
| 20/2/1/0/0.1 | 14.7 | 1.1 |
| 20/2/1/0.5/0.1 | 11.9 | 1.25 |

In Vitro Cytotoxicity Tests
Cell Culture

CT26 cell line (American Type Culture Collection (ATCC, CRL-2638, LGC Standards, Molsheim, France) were used for the in vitro experiments. CT26 cells were originally obtained from an undifferentiated colon carcinoma chemically induced by N-nitroso-N-methylurethan that was later cloned to obtain the stable CT26 cell line. This cell line was used for in vivo evaluation.

For the evaluation of cytotoxicity we used another type of cancer cell A2780 ovarian carcinoma cell line provided by ECACC (93112519 SIGMA, human cell Line).

All of these tumor cell were cultured at 37° C. in a 5% $CO_2$-humidified atmosphere. Dulbecco's Modified Eagle Medium (DMEM, Gibco) was used for CT26 cell line and RPMI-1640 Medium with sodium bicarbonate and 2 mM of glutamine (RPMI, Gibco) was used for A2780 cell line. These medium was supplemented by 10% fetal bovine serum (FBS, Gibco Life technologies), 100 µM of streptomycin, and 100 U/mL of penicillin. If not mentioned otherwise, this mix will be simplified as cell culture medium.

Cell Adhesion Evaluation

Different hydrogel (300 µl) was put into 24 well plate during 10 minutes at 4° C. The plate was incubated at 37° C., 30 min in order to assure the gelification process. A suspension of cell was seeded into the hydrogel (A2780: 800 000 cellules/ml), the cell in contact with hydrogel was incubated for 24 h à 37° C. After this overnight incubation a picture of the cell was made. The adhesive cell was then isolated with trypsine 0.05% and the cell suspension was counted with KOVA® GLASSTIC® slide. The percent of adherent cell was calculated as a function of control (the cells who adhere to the plastic plate directly).

Cytotoxicity Evaluation

The cell were seeded in Falcon™ Cell Culture Inserts (Cyclopore® Falcon® 353095) for 24 h at 37° C. (400 000 cell per insert in 500 µl of medium). At day 2, the apical medium was removed and 200 µL of hydrogel or control solution was put on the insert. At day 3, photography was realized after 24 hours of incubation with hydrogel or control solution. The plate were incubated at 4° C. during ten minutes, in order to liquefied the gel and the wells were wash two time with culture medium, to removed dead cell and hydrogel residue. A solution of the 3-(4,5-Dimethylthiazol-2-yl)-2,5-diphenyltetrazolium bromide (MU, Sigma Aldrich, 298-93-1; 0.5 mg/ml) in culture medium was incubated with the cell during 4 h. The solution was removed and replaced by 100 µL of Dimethyl sulfoxide DMSO and the plate was shaken during 10 min. The absorption was subsequently measured at 562 nm. In a 96-well plate (TPP Techno Plastic Products, 92024). The viability was estimated in percent of absorbance of the control wells.

In Vivo Anti-Tumour Activity

Mice model. The experiments were carried out in Balb/CJRJ female mice (Janvier, St Genest de Lisle, France), aged from 6 to 7 weeks. Animal experiments were conducted according to European and national guidelines and were approved by the institutional ethics committee.

Tumor Implantation into Mice: Colorectal Cancer Peritoneal Carcinomatosis CRPC Model As tumour model, a modified cell line of the CT26 cell line was used, the CT26-luc cell line. CT26-luc cells in culture medium were injected intraperitoneally ($5 \times 10^5$ CT26-luc cell in 1 ml per mice).

Thermogel Insertion. 6 days after tumour injection the mice were anaesthetized (isofuran 2.0%) and small incision of 1-2 cm was made in the skin and the muscular plane. During the anaesthesia the mouse was kept at physiologic temperature. The hydrogel formulations P407/P188/Alginate/5 Fu/oxaliplatin 20/2/1.0.5/0.3 or P407/P188/Alginate solution was injected with 1 ml syringe. The wound was closed with silk thread 5.0.

Tumor Follow-up. The diffusion of the tumour in the peritoneal cavity was measured by optical imaging. The mice were therefore injected intraperitoneally 20 min before imaging with 2 mg luciferin (200 µl, 10 mg/ml) (Dluciferin K salt, INTERCHIM). By reacting with luciferase a photon signal is produced which can be detected by the camera (PhotonlMAGER™ Biospace Lab). The mice were thus imaged during 10 min while being under anaesthesia with isoflurane. Image analysis was performed with the M3 Vision software developed by Biospace Lab.

II Results

In Example 2, the formulation range is broadened, with examples of P407/P188 17/1, 20/1 and 20/5 in which various gelling agent were added such as alginate, xantham gum, carbopol, chitosan.

Designed formulations to obtain a targeted gelification temperature (Tg) between 26 and 37° C. All the formulations tested containing both copolymer P407/P188 and a gelling agent are thermogels which respond to the fixed temperature target. The mechanical resistance of the gel was obtained via rheological measurement of the gel elasticity G'. The release kinetic of the active substance was obtained by the rheological measurement of both the gel elasticity G' and the viscosity, followed by the calculation of tan δ reflecting a slower release when the value tends to zero. As a general feature, we observed that an increase of the concentration of the gelling agent improved the expected properties of the gel, such as mechanical resistance and increased retention of the active substance within the gel.

Example 2 shows that shear thinning thermogels may be obtained by incorporating aerosil.

Viscosity increases when the aerosil is added to the formulations, from 85.78 mPa·s for the formulation based on 17% of P407 and 1% of P188 to 95.12 mPa·s when 2% of aerosil is added, and from 122 mPa·s for the formulation based on 20% of P407 and 2% of P188 to 156.54 mPa·s when 2% of aerosil is added to the formulation (Table 2). The impact of the insertion of aerosil in the various formulations of the copolymers P407/P188 clearly show a reduced G" with a maintained mechanical strength indicating a shear thinning increased which will be favorable to the injection and pulverisation of the hydrogel. The study of average curves for a shear rate from 0 to 10 s-1 shows that the shear thinning increase with the aerosil concentration (Table 2).

It was also shown that adhesive hydrogels may be obtained by the incorporating increasing amounts of alginate within P407/P188 20/2.

Figure 12:
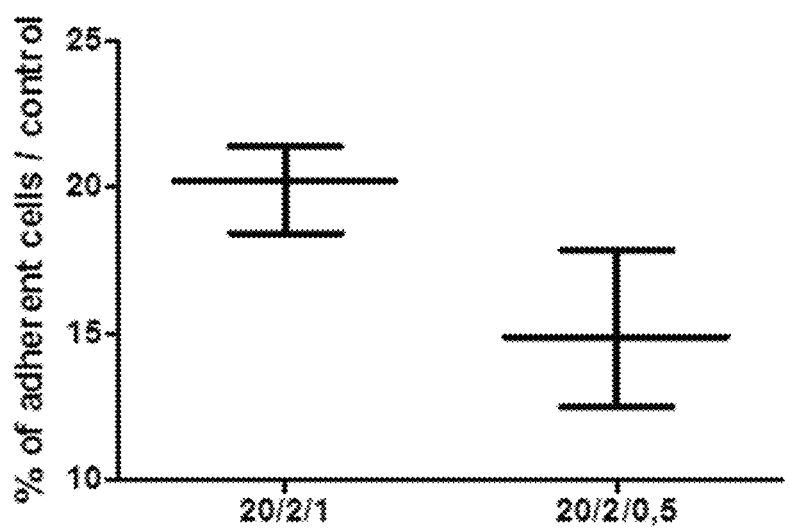
FIG. 12 represents the influence of the addition of alginate (0.5 and 1%) in thermogels of the invention containing P407/P188 (20/2) on the adhesion of the cell. The percent of adherent cell was calculated as a function of control (the cells which adhere to the plastic plate directly).

The adhesive effect of the formulation was shown by loading cells on a standard plate or on a plate covered by a gel containing P407/P188 20/2 with 0.5 or 1% of alginate. The percentage of adhesion shows that the alginate has an adhesive effect as the cells were able to attach and grow on the gel in particular if the percentage of alginate is increased (FIG. 12).

In Example 2, the anticancer agents used are 5-fluorouracil, oxaliplatin and a combination thereof. Example 2 further provides DSC measurements showing that the anticancer agents did not modify the cohesion of the gels, an in vitro toxicity study on an ovarian cell line showing that the anticancer agents are still active even if initially embedded within the gel, and an in vivo post-treatment reduction of metastases in mice bearing intraperitoneal metastases.

The thermal analyses by DSC showed that the drugs did not impair the formation of the gel. Depending on the initial mixture of the copolymers, a stabilization of the gel could be obtained.

Figure 13:
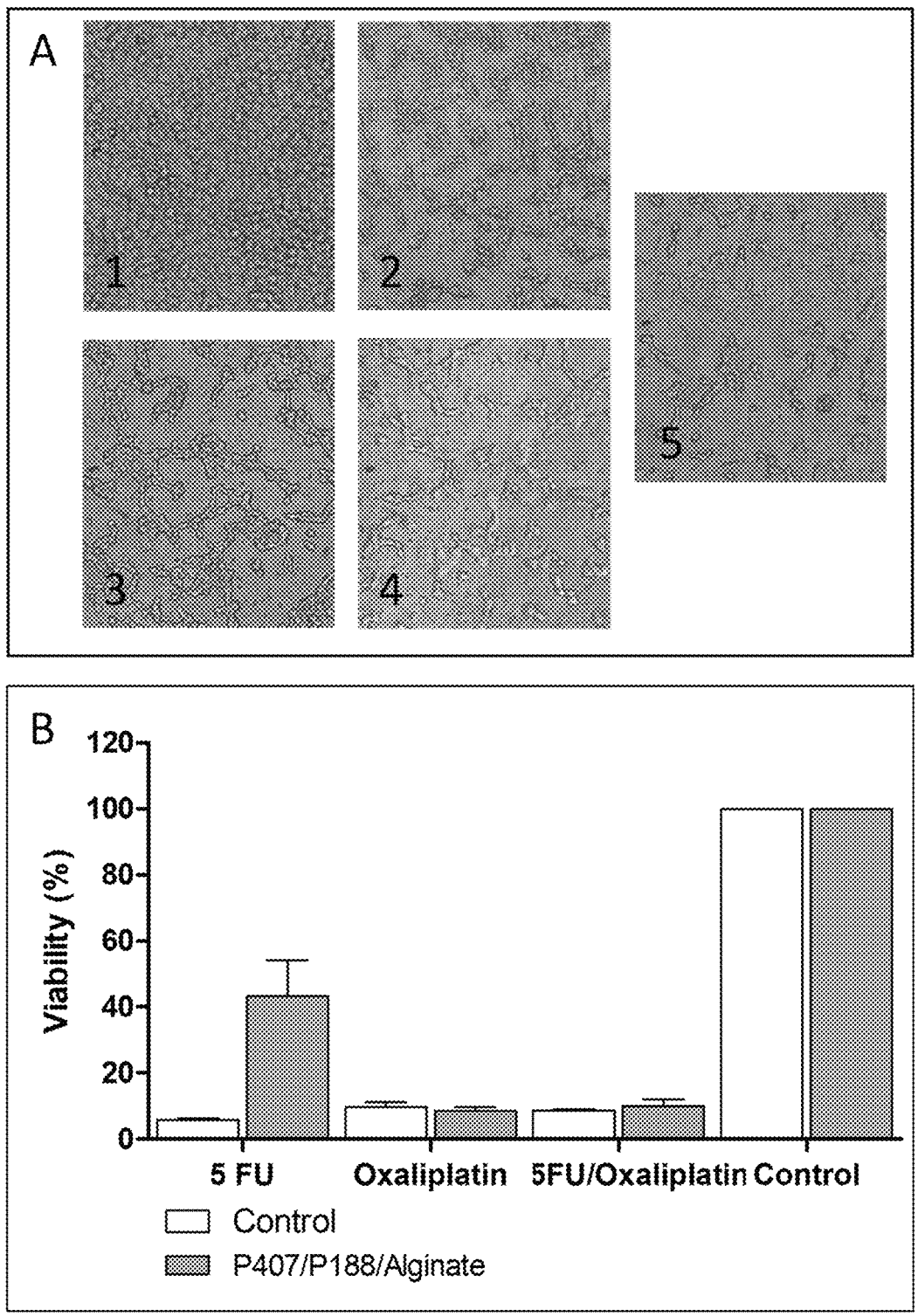
FIG. 13 represents the cytotoxicity of gels containing 5-FU, oxaliplatin or the combinaison 5-FU and oxaliplatin, on ovarian cell line A2780.

The cytotoxicity of the gel P407/P188/Alginate 20/2/1 containing 5 fluorouracil (0.5 mg), oxaliplatin (0.1 mg) or both 5 fluorouracil (0.5 mg) and oxaliplatin (0.1 mg) showed that the ovarian cells A2780 were sensitive to the individual drug or the combination of the anticancer agents embedded within the gel and reached similar levels of cytotoxicity as a solution of the anticancer agents (FIG. 13).

Figure 14:
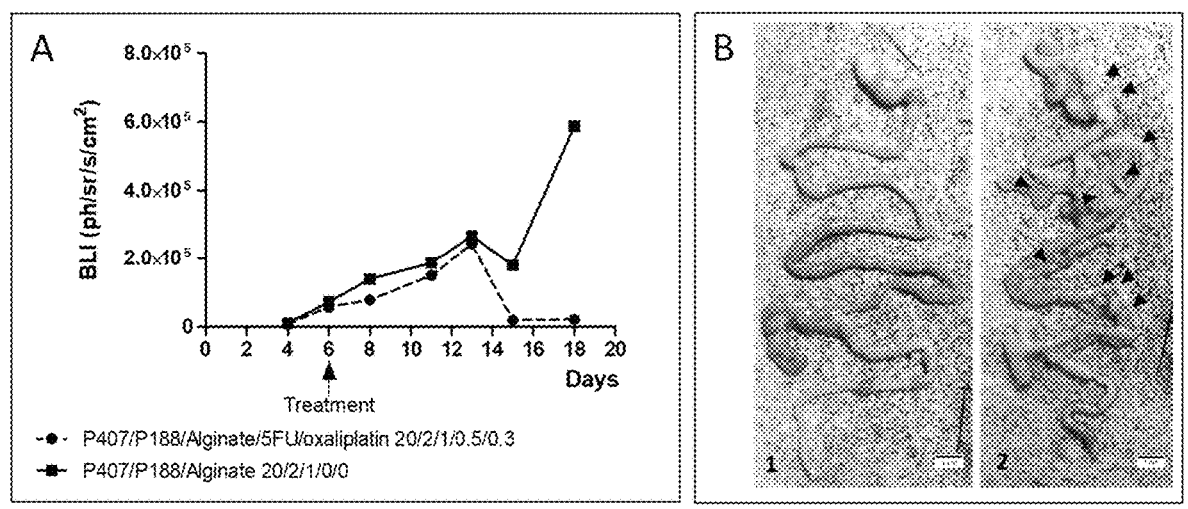
FIG. 14 represents the evaluation of in vivo efficacy of 5-FU oxaliplatine containing hydrogel P407/P188/alginate/5 FU/OX 20/2/1.0.5/0.3 on colorectal peritoneal carcinomatosis CT26.

A model of intraperitoneal carcinosis was set up to evaluate the impact of the gel P407/P188/alginate containing the mixture of 5-fluorouracil and oxaliplatin (5 mg and 3 mg respectively) on the metastases in vivo. The follow-up on one mouse is shown: the metastases growth observed by bioluminescence (luciferase activity) shows an increase of the tumors than a decrease solely for the mice treated with the gel containing the combination of anticancer agents. The observation of the metastases post-mortem shows a strong reduction of the number of metastases within the intestine for the mice treated with the gel containing 5 Fluorouracil and oxaliplatin (FIG. 14).

The invention claimed is:

1. Gelling composition consisting of:
   12 wt % to 30 wt % of at least a poloxamer or mixture of poloxamers, relative to the total weight of the composition;
   0.01 wt % to 10 wt % of at least a gelling agent relative to the total weight of the composition; and
   0.1 wt % to 10 wt % of at least an anticancer agent,
   water,
   optionally one or more rheofluidizing agent(s), pharmaceutically acceptable excipient(s), stabilizer(s) or preservative(s), and
   optionally one or more another therapeutic agent,
   wherein the gelling agent is selected from the group consisting of chitosan and derivatives thereof, carrageenan and derivatives thereof, alginate and derivatives thereof, pectin and derivatives thereof, fibrin and derivatives thereof, homo- and copolymers of acrylic acid crosslinked with a polyalkenyl polyether, or mixtures thereof,
   wherein the optional pharmaceutically acceptable excipient is selected from the group consisting of propylene glycol, salts or bioadhesive agents selected from hydroxypropyl methylcellulose, methylcellulose or cross-linked acrylic acid polymers,
   wherein the optional stabilizer is selected from the group consisting of surfactants, polymers, polyols, a poloxamer, albumin, gelatin, trehalose, proteins, sugars, polyvinylpyrrolidone, N-acetyl-tryptophan ("NAT"), caprylat, a polysorbate, amino acids, and divalent metal cations,
   wherein the optional preservative is selected from the group consisting of benzyl alcohol, cresols, benzoic acid, phenol, parabens and sorbic acid,
   wherein the gelling composition is a homogenous aqueous gelling composition, and
   wherein the gelling composition is in the form of a spray, an injectable solution, or a spreadable solution.

2. The gelling composition of claim 1, wherein the gelling temperature of the composition is of between 20° C. and 40° C.

3. The gelling composition of claim 1, wherein the gelling agent is selected from the group consisting of alginate, pectin and fibrin or mixtures thereof.

4. The gelling composition of claim 1, wherein the anticancer agent is selected from the group consisting of 5-FU (fluorouracil), oxaliplatin, cisplatin, folinic acid, irinotecan, metformin, paclitaxel, topotecan, etoposide, ifosfamide, altretamine, doxorubicin, tamoxifen, tamoxifen citrate, gemcitabine and mixtures thereof, or a mixture of 5-FU and cis-platin, a mixture of 5-FU and oxaliplatin, a mixture of 5-FU and folinic acid, a mixture of 5-FU, folinic acid and oxaliplatin, a mixture of oxaliplatin and paclitaxel or a mixture of cisplatin and paclitaxel.

5. The gelling composition of claim 1, wherein the rheofluidizing agent is present in the composition.

6. The gelling composition of claim 1, wherein the one or more therapeutic agents are selected from the group consisting of 5-FU (fluorouracil), oxaliplatin, cisplatin, folinic acid, irinotecan, metformin, paclitaxel, topotecan, etoposide, ifosfamide, altretamine, doxorubicin, tamoxifen, tamoxifen citrate, gemcitabine and mixtures thereof, or a mixture of 5-FU and cis-platin, a mixture of 5-FU and oxaliplatin, a mixture of 5-FU and folinic acid, a mixture of 5-FU, folinic acid and oxaliplatin, a mixture of oxaliplatin and paclitaxel or a mixture of cisplatin and paclitaxel, wherein the one or more therapeutic agent are different from the anticancer agent.

* * * * *